（12）United States Patent
Tsukahara et al.

(10) Patent No.: US 11,307,176 B2
(45) Date of Patent: Apr. 19, 2022

(54) STANDARD-MOISTURE GENERATOR, SYSTEM USING THE STANDARD-MOISTURE GENERATOR, METHOD FOR DETECTING ABNORMALITY IN STANDARD-MOISTURE AND COMPUTER PROGRAM PRODUCT FOR DETECTING THE ABNORMALITY

(71) Applicant: Ball Wave Inc., Sendai (JP)

(72) Inventors: Yusuke Tsukahara, Sendai (JP); Osamu Hirayama, Sendai (JP); Nobuo Takeda, Sendai (JP); Toshihiro Tsuji, Sendai (JP); Kazushi Yamanaka, Sendai (JP); Toru Oizumi, Sendai (JP); Hideyuki Fukushi, Sendai (JP); Nagisa Sato, Sendai (JP); Shingo Akao, Sendai (JP); Tatsuhiro Okano, Sendai (JP)

(73) Assignee: Ball Wave Inc., Sendai (JP)

( * ) Notice: Subject to any disclaimer, the term of this patent is extended or adjusted under 35 U.S.C. 154(b) by 20 days.

(21) Appl. No.: 16/968,415

(22) PCT Filed: Feb. 12, 2019

(86) PCT No.: PCT/JP2019/004833
§ 371 (c)(1),
(2) Date: Aug. 7, 2020

(87) PCT Pub. No.: WO2019/156255
PCT Pub. Date: Aug. 15, 2019

(65) Prior Publication Data
US 2020/0400619 A1    Dec. 24, 2020

Related U.S. Application Data

(60) Provisional application No. 62/629,246, filed on Feb. 12, 2018.

(51) Int. Cl.
*G01N 29/22*  (2006.01)
*G01N 29/02*  (2006.01)
*G01N 29/34*  (2006.01)

(52) U.S. Cl.
CPC ......... *G01N 29/222* (2013.01); *G01N 29/022* (2013.01); *G01N 29/343* (2013.01);
(Continued)

(58) Field of Classification Search
CPC .. G01N 29/222; G01N 29/022; G01N 29/343; G01N 29/2462; G01N 2291/0256;
(Continued)

(56) References Cited

U.S. PATENT DOCUMENTS 3,665,748 A   5/1972   Mator
4,849,174 A   7/1989   Brandt et al.
(Continued)

FOREIGN PATENT DOCUMENTS

JP    S59-092841 U    6/1984
JP    S60-011160 A    1/1985
JP    H01-221646 A    9/1989

OTHER PUBLICATIONS

N. Takeda, et al., "Extremely Fast 1 μmol·mol-1 Water-Vapor Measurement by a 1mm Diameter Spherical SAW Device", Int. J. Thermophys., 2012, pp. 1642-1649, vol. 33, Springer; Cited in the specification.

(Continued)

*Primary Examiner* — Suman K Nath
(74) *Attorney, Agent, or Firm* — Metrolex IP Law Group, PLLC

(57) ABSTRACT

A standard-moisture generator includes a flow controller configured to control a flow of a gas, a dryer connected to the flow controller, configured to absorb water molecules in the gas and to generate a dry gas having a background (Continued)

moisture, a moisture cell connected to the dryer, configured to add an object moisture to the dry gas, and a delay member connected to the moisture cell, configured to pass the dry gas with a delay time depending on a concentration of the background moisture in the dry gas.

9 Claims, 18 Drawing Sheets

(52) U.S. Cl.
CPC ............ *G01N 2291/0256* (2013.01); *G01N 2291/02845* (2013.01); *G01N 2291/0423* (2013.01)

(58) Field of Classification Search
CPC . G01N 2291/02845; G01N 2291/0423; G01N 2291/021; G01N 2291/02425; G01N 33/0006; F24F 3/167; F24F 11/0008; F24F 2110/20
See application file for complete search history.

(56) References Cited

U.S. PATENT DOCUMENTS

| | | | |
|---|---|---|---|
| 5,294,378 A | | 3/1994 | Succi et al. |
| 5,802,862 A | * | 9/1998 | Eiermann ............... F24F 3/14 165/228 |
| 6,526,803 B1 | | 3/2003 | Fraenkel et al. |
| 9,849,024 B2 | * | 12/2017 | Mandel ................. A61F 7/007 |

OTHER PUBLICATIONS

Toshihiro Tsuji, et al., "Temperature compensation of ball surface acoustic wave sensor by two-frequency measurement using undersampling", Japanese Journal of Applied Physics, 2015, vol. 54, 07HD13, The Japan Society of Applied Physics; Cited in the specification.

Hisashi Abe et al., "Performance evaluation of a tracemoisture analyzer based on cavity ringdown spectroscopy: Direct comparison with the NMIJ trace-moisture standard", Sensors and Actuators A: Physical, Feb. 2011, pp. 230-238, vol. 165, Issue 2; Cited in the specification.
Gerard McKeogh et al., "The Proper Mechanism for Field Validating Moisture Analyzers GAS 2017", presented at the GAS2017; Cited in the specification.
Hisashi Abe et al., "Development of humidity standard in trace-moisture region: Characteristics of humidity generation of diffusion tube humidity generator", Sensors and Actuators A: Physical, 2006, pp. 202-208, 201; Cited in the specification.
M Stevens et al., "The NPL standard humidity generator: an analysis of uncertainty by validation of individual component performance", Measurement Science and Technology, 1992, pp. 943-952, vol. 3, British Crown; Cited in the specification.
Andrew E. O'Keeffe et al., "Primary Standards for Trace Gas Analysis", Analytical Chemistry, May 1966, p. 760-763, vol. 38, No. 6; Cited in the specification.
Tadahiro Ohmi, "Ultra clean processing", Microelectronic Engineering, 1991, pp. 163-176, 10; Cited in the specification.
Tadahiro Ohmi et al., "Formation of chromium oxide on 316L austenitic stainless steel", Jounal of Vacuum Science & Technology A, Jul./Aug. 1996, pp. 2505-2510, 14(4), American Vacuum Sociemty; Cited in the specification.
Toshihiro Tsuji, et al., "Moisture adsorption desorption characteristics of stainless steel tubing measured by ball surface acoustic wave trace moisture analyzer", Japanese Journal of Applied Physics, 2017, vol. 56, 07JC03, The Japan Society of Applied Physics; Cited in the specification.
A Jaulmes et al., "Study of Peak Profiles in Nonlinear Gas Chromatography. 1. Derivation of a Theoretical Model", J. Phys. Chem., 1984, pp. 5379-5385, 88, American Chemical Society; Cited in the specification.
A Jaulmes et al., "Study of Peak Profiles in Nonlinear Gas Chromatography. 2. Determination of the Curvature of Isotherms at Zero Surface Coverage on Graphitized Carbon Black", J. Phys. Chem., 1984, pp. 5385-5391, 88, American Chemical Society; Cited in the specification.
Extended European Search report ("EESR") dated Sep. 23, 2021 in a counterpart European Application.

* cited by examiner

[FIG. 1]
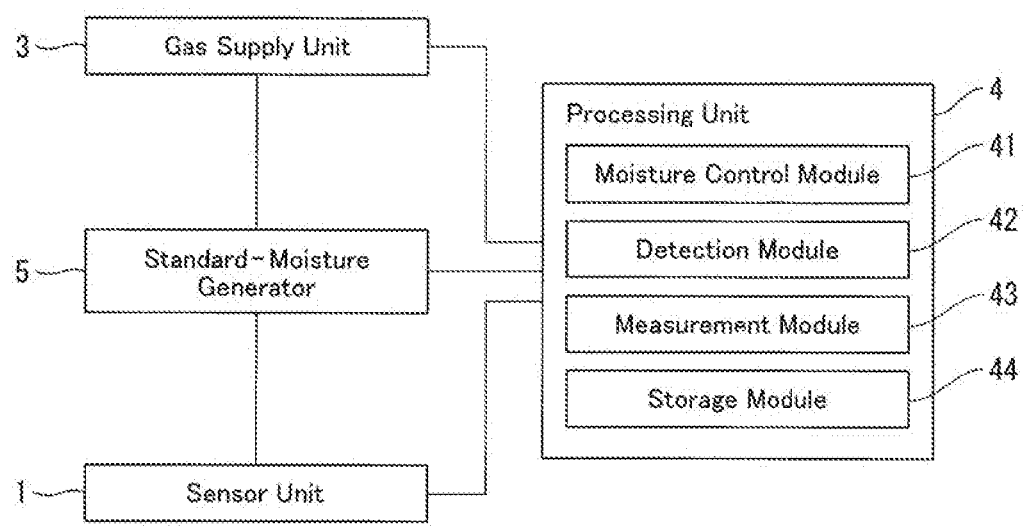

[FIG. 2]
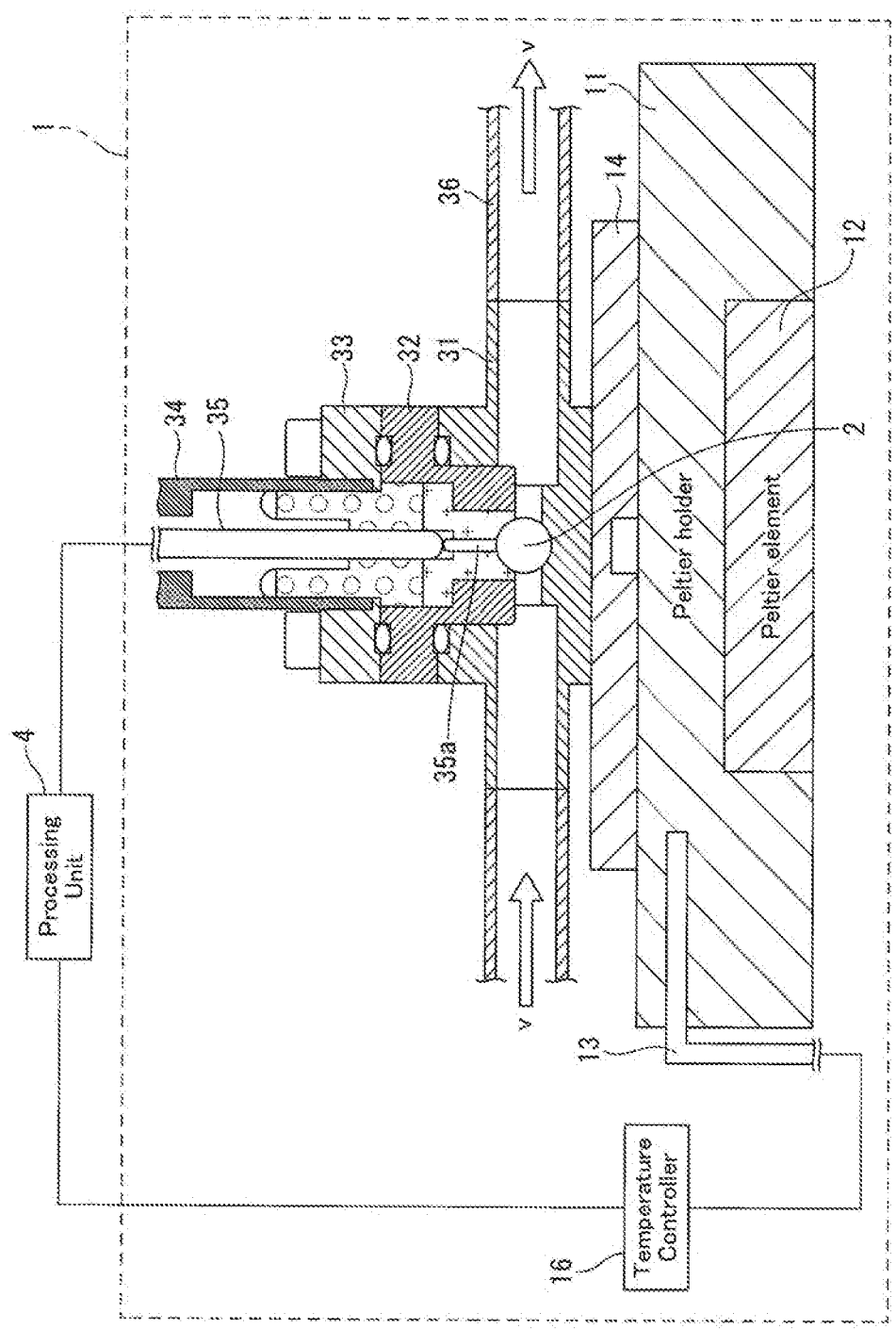

[FIG. 3]
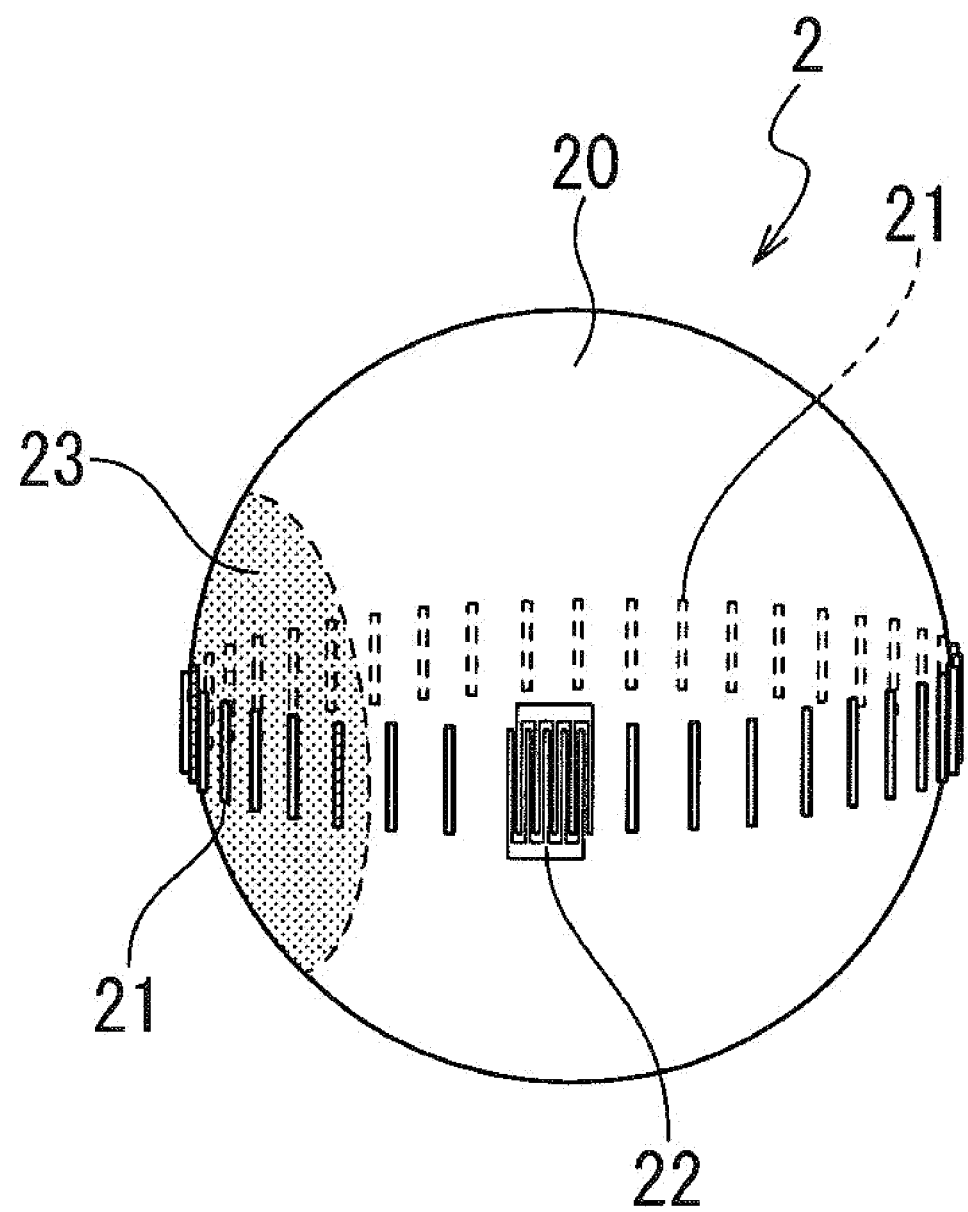

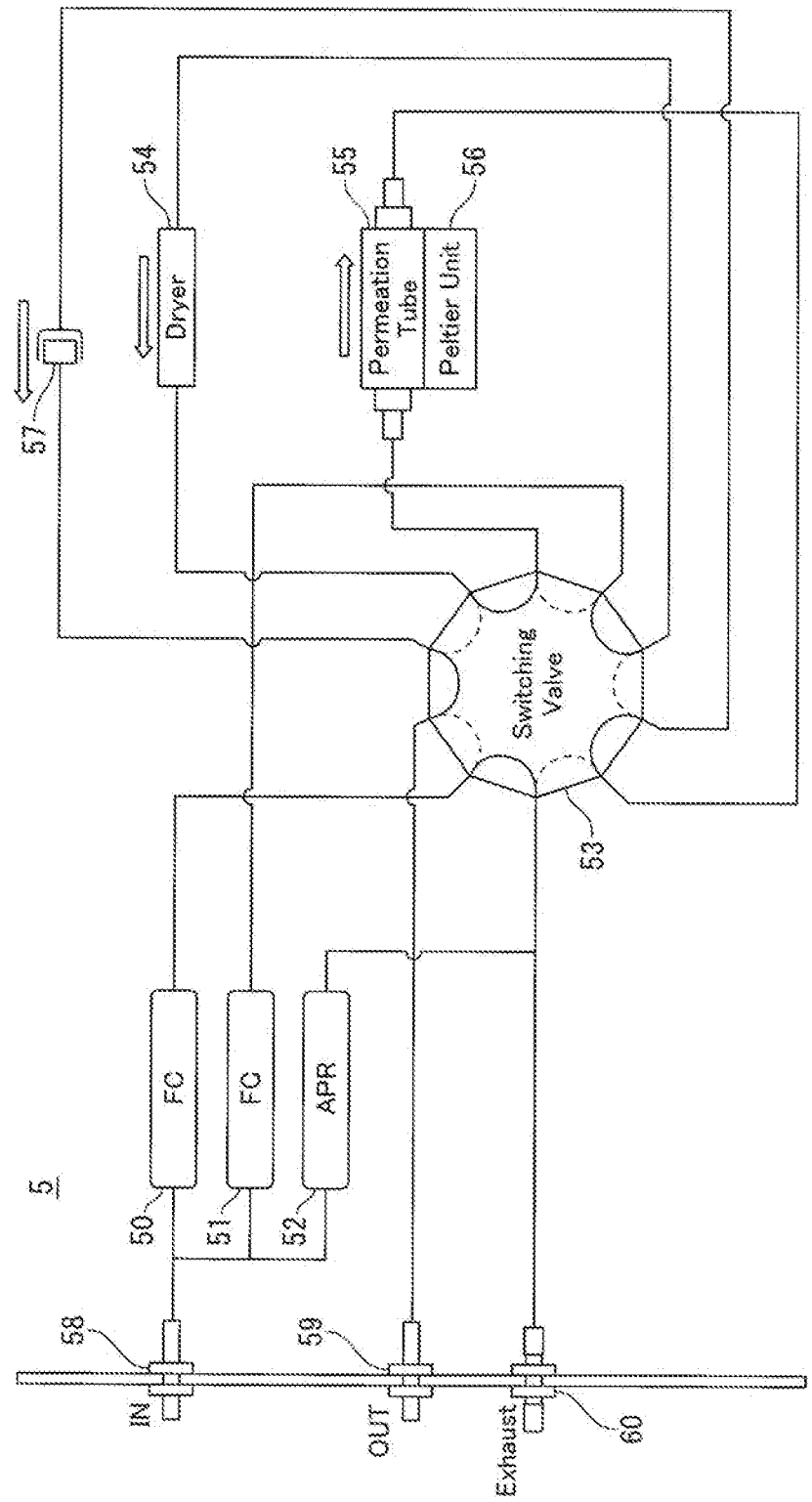
[FIG. 4]

[FIG. 5]
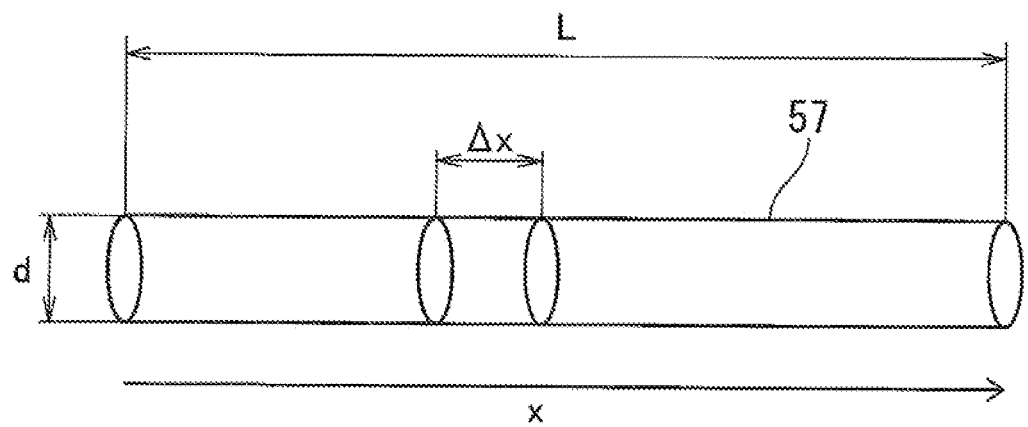
[FIG. 6]
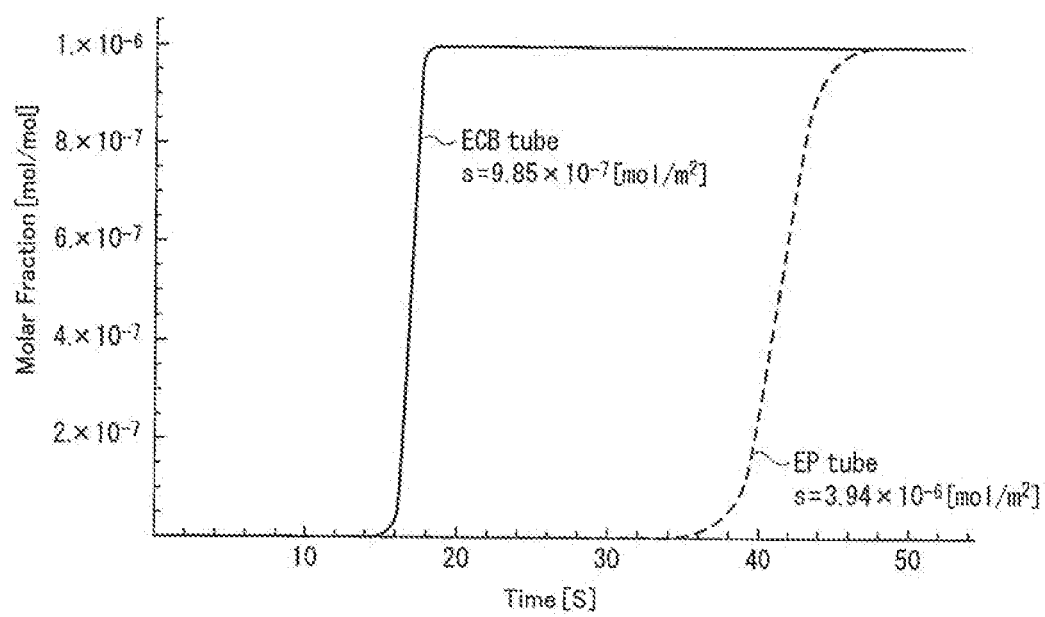

[FIG. 7]
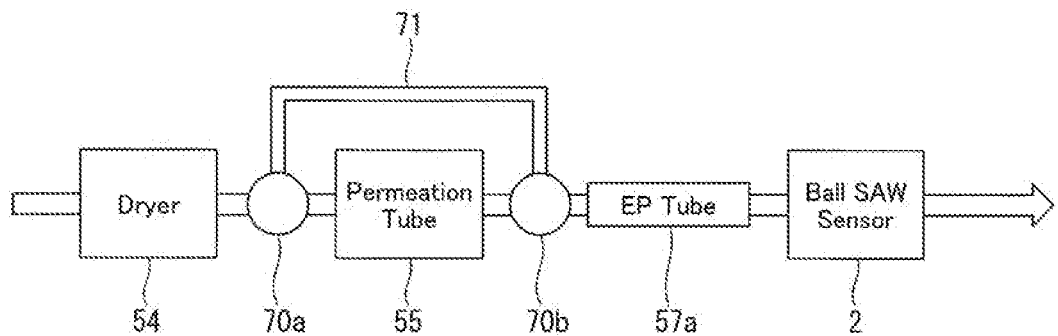
[FIG. 8]
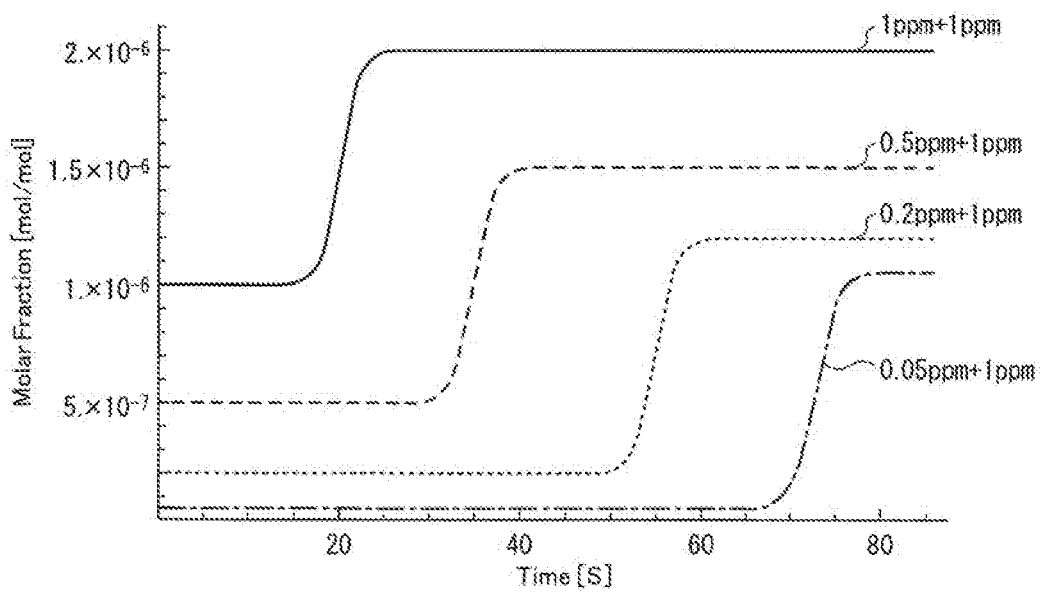

[FIG. 9]
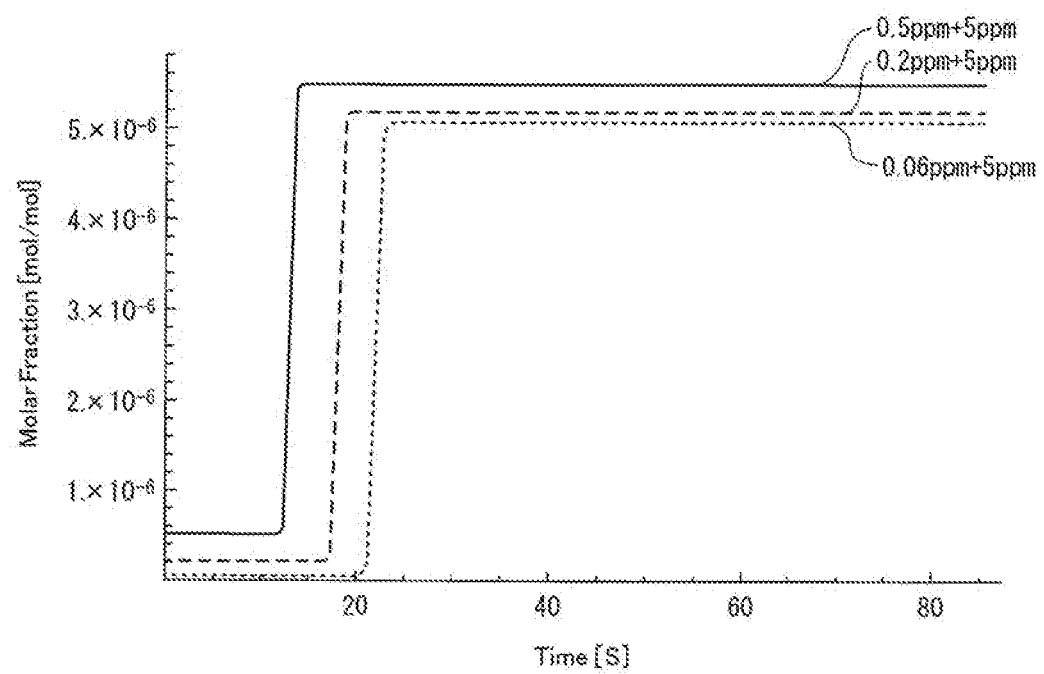

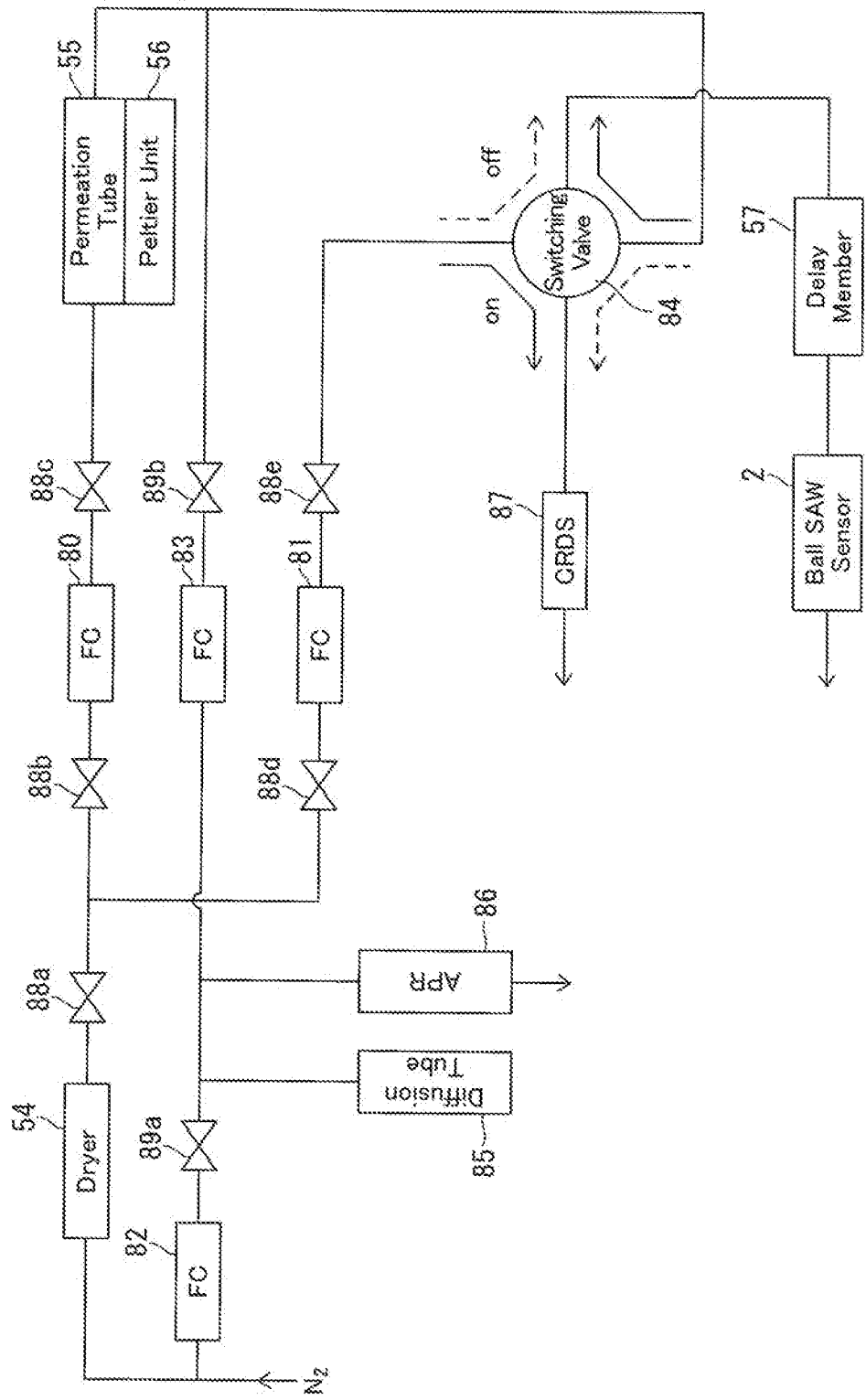
[FIG. 10]

[FIG. 11]
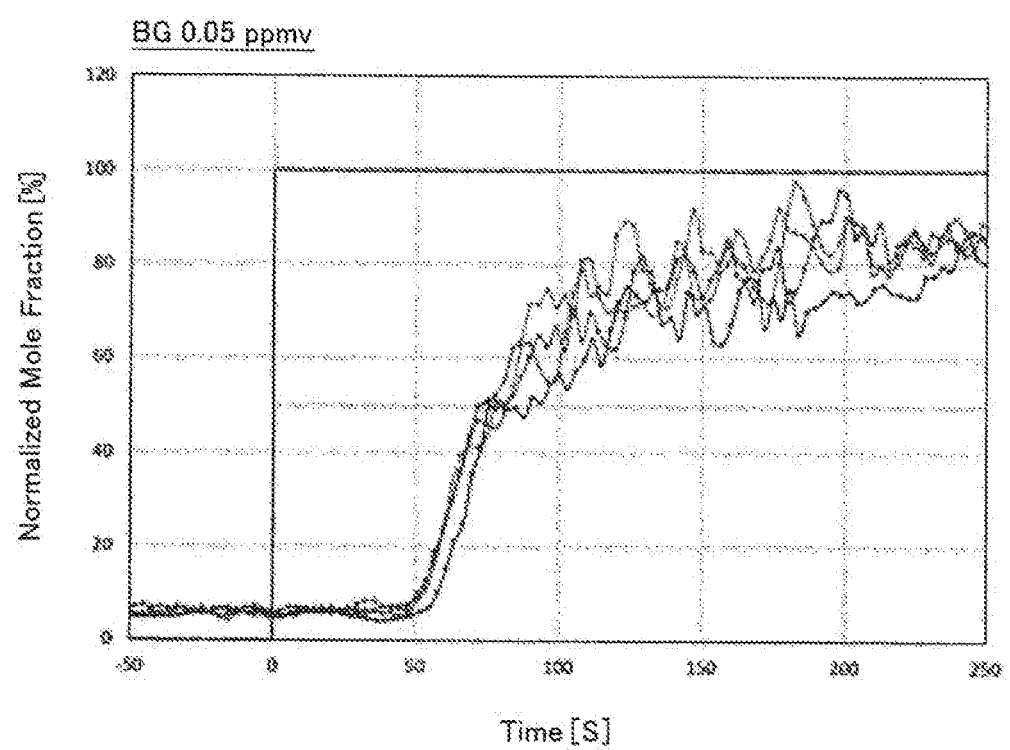

[FIG. 12]
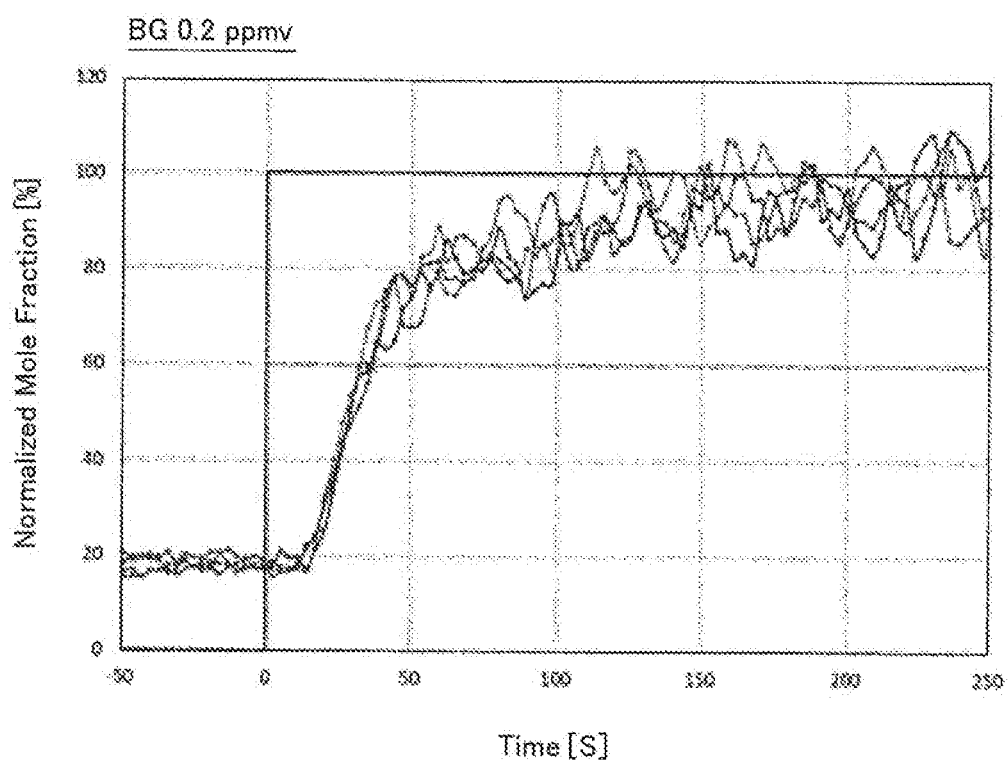

[FIG. 13]
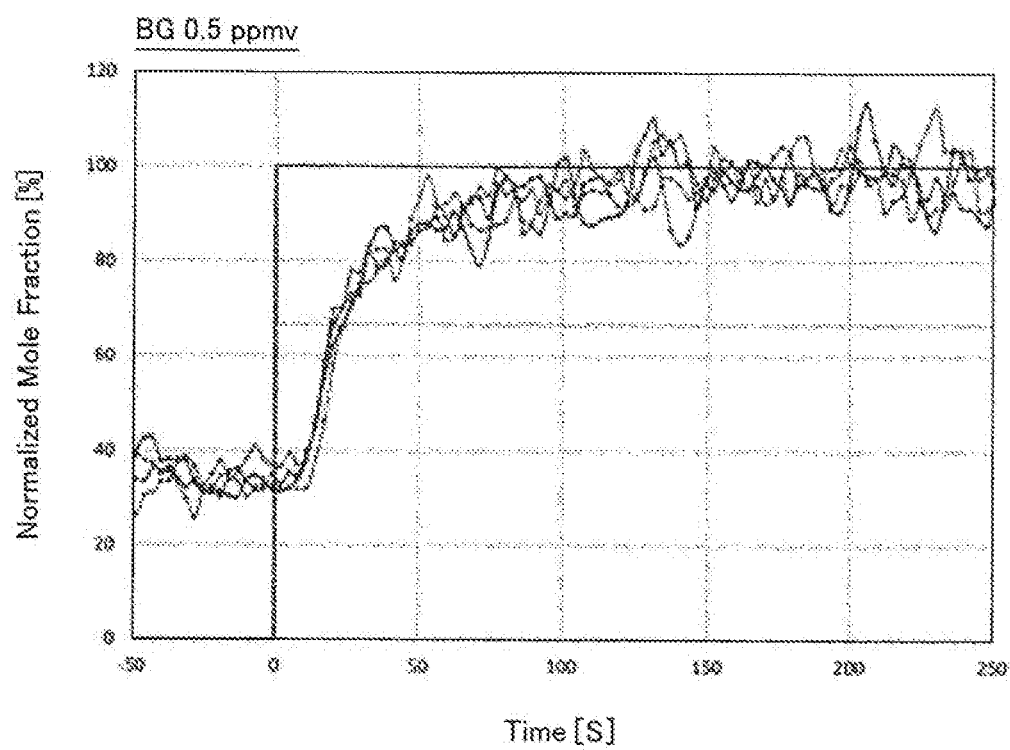

[FIG. 14]
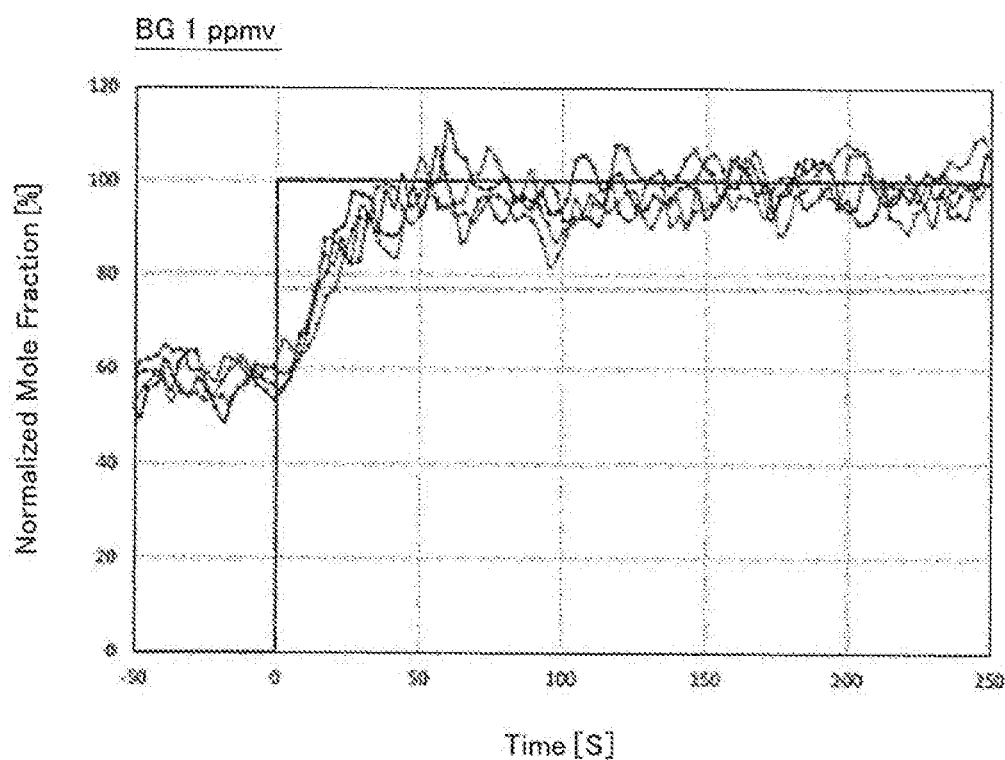

[FIG. 15]
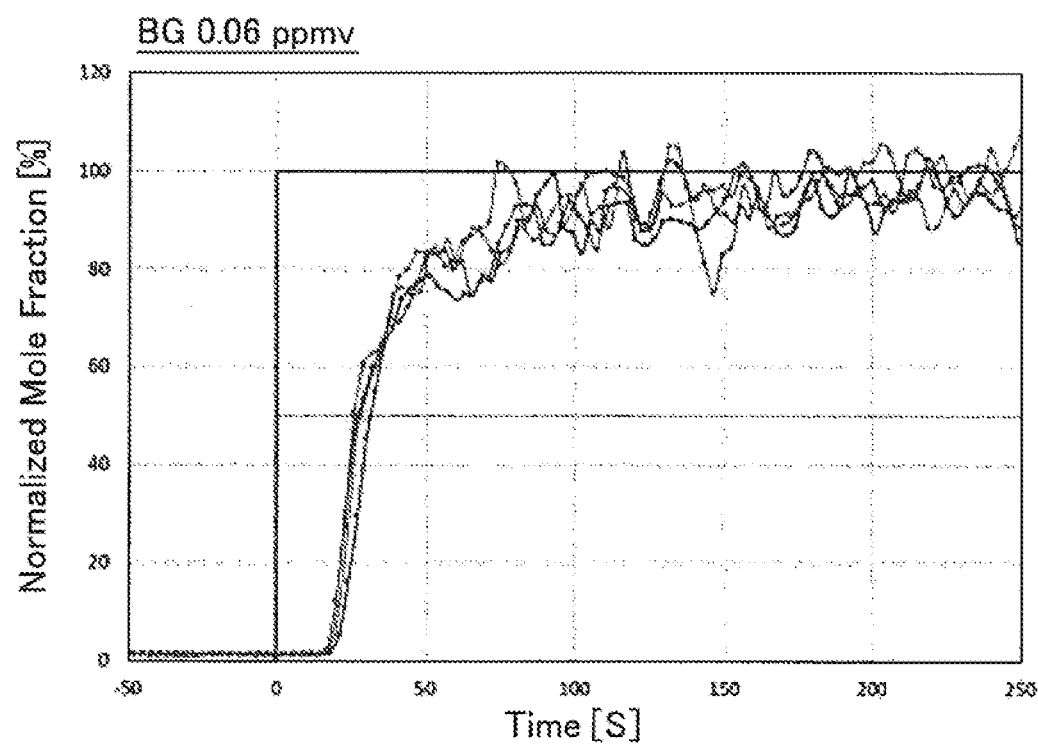

[FIG. 16]
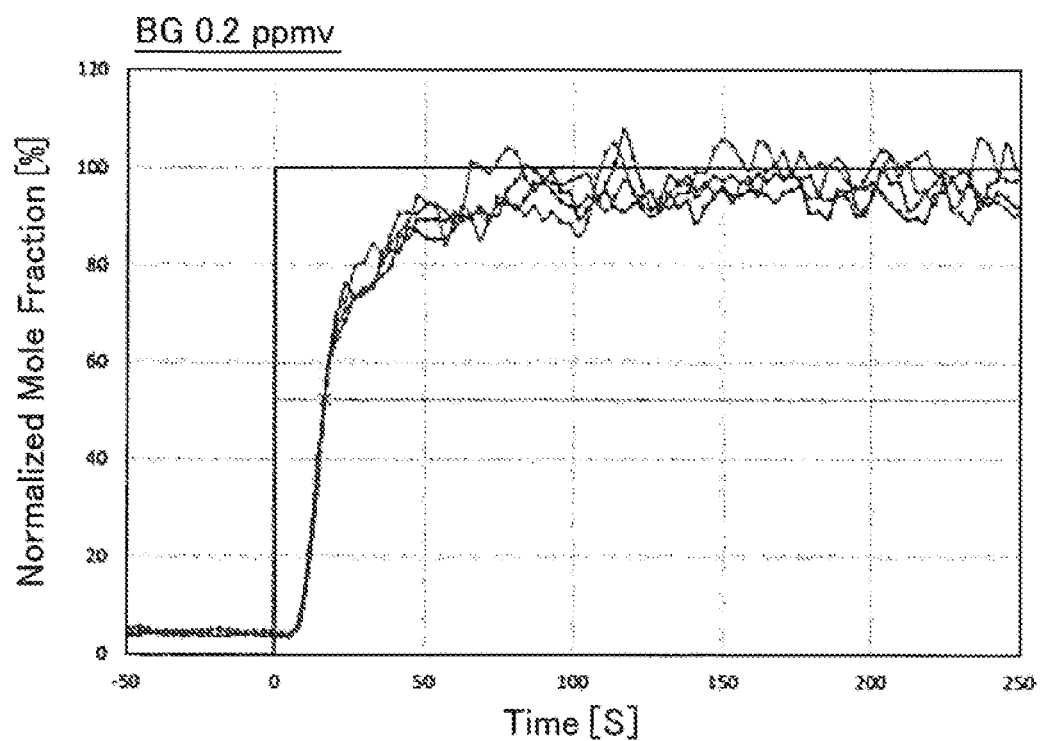

[FIG. 17]
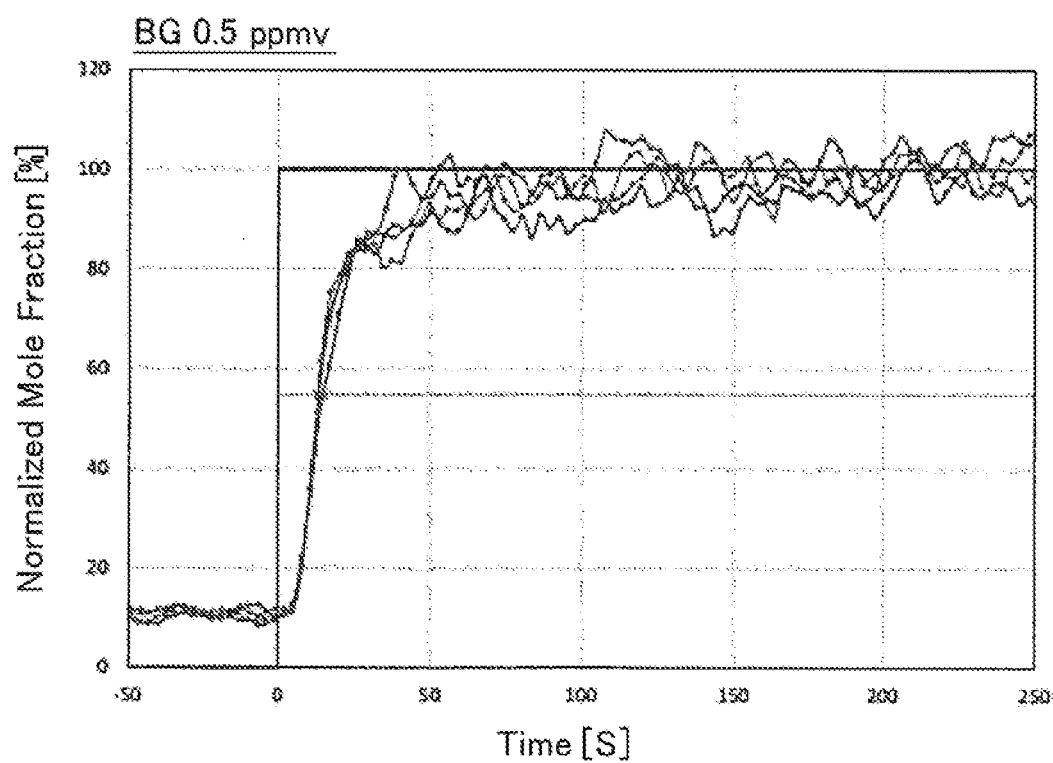

[FIG. 18]
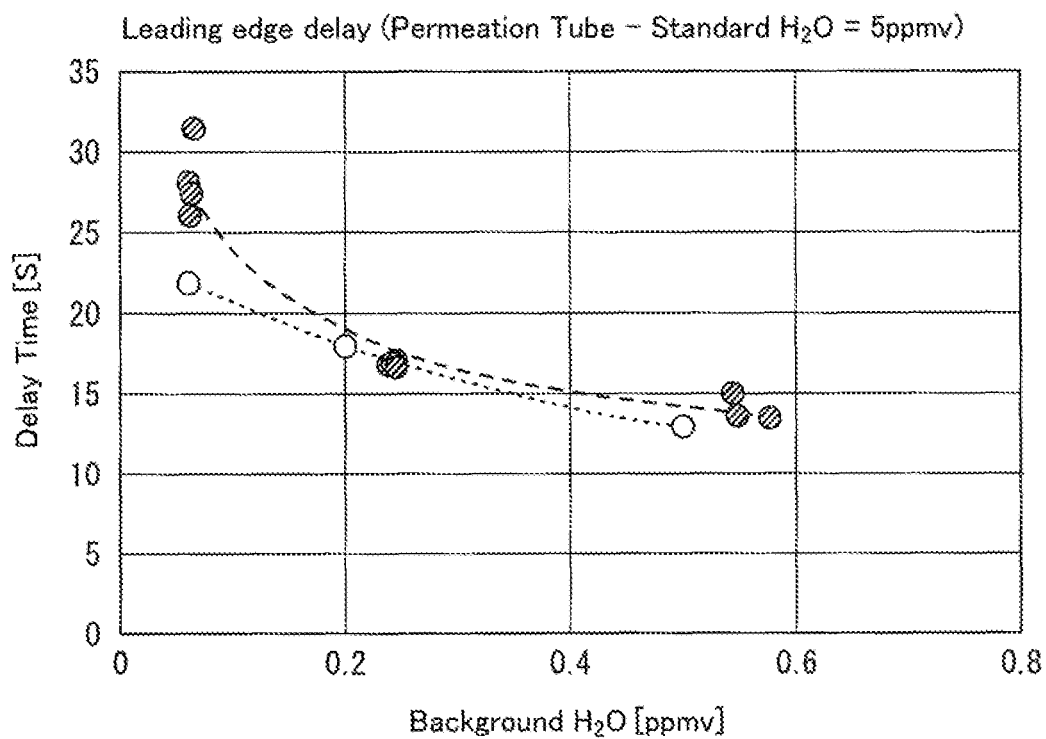
[FIG. 19]
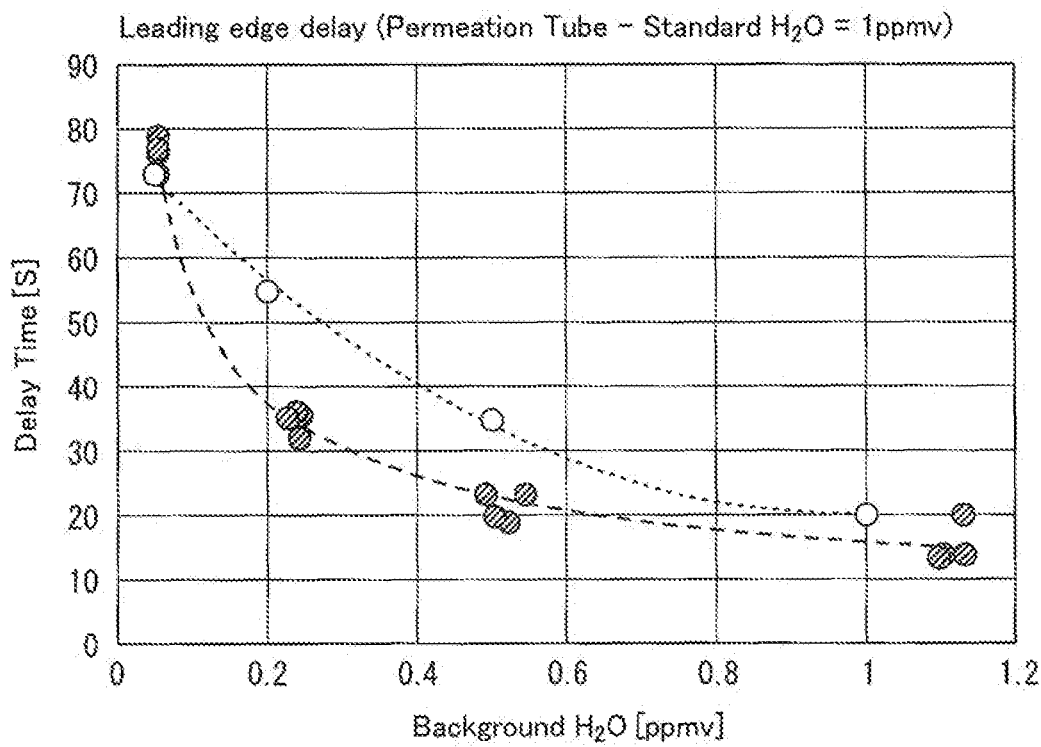

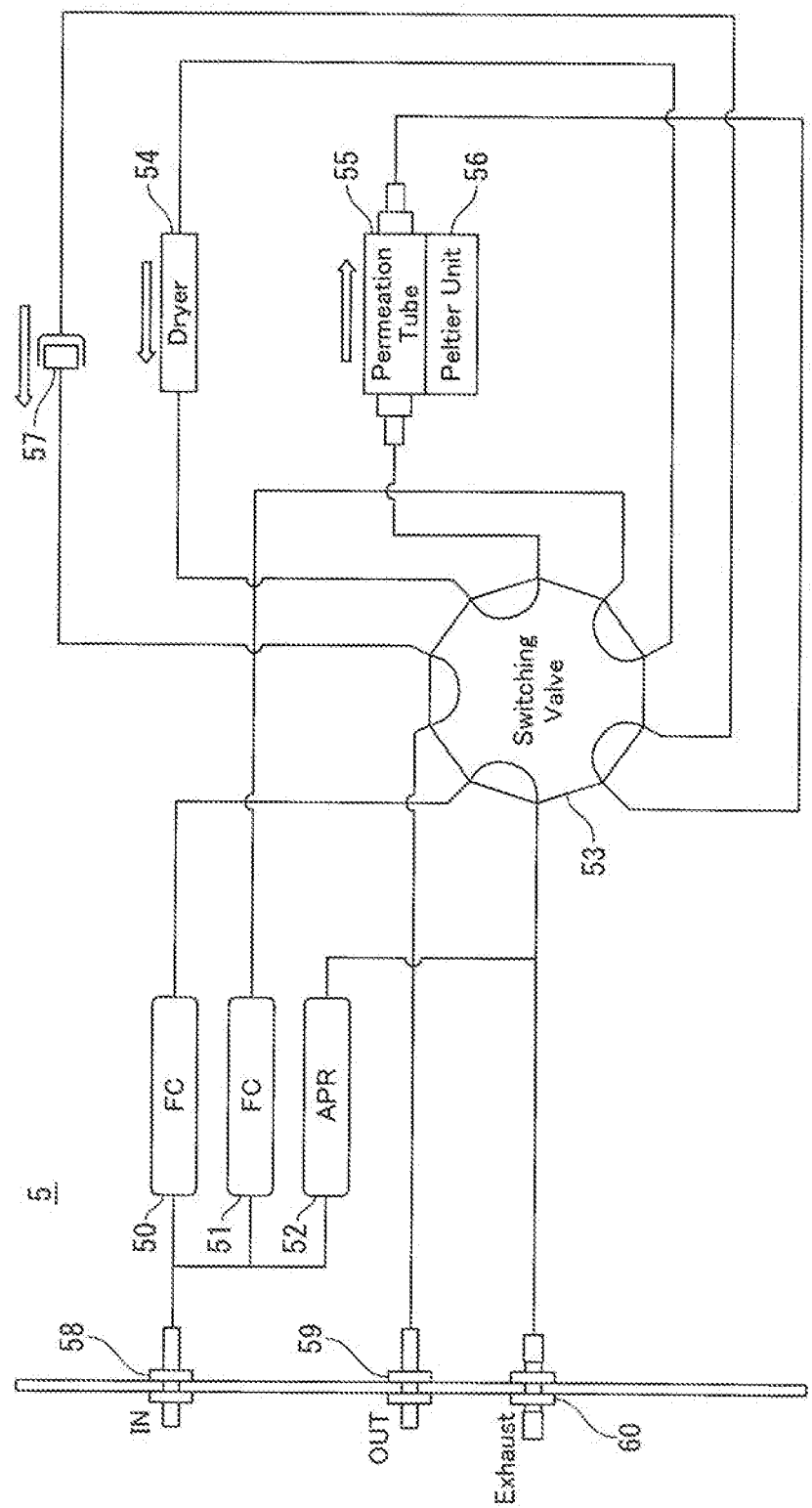
[FIG. 20]

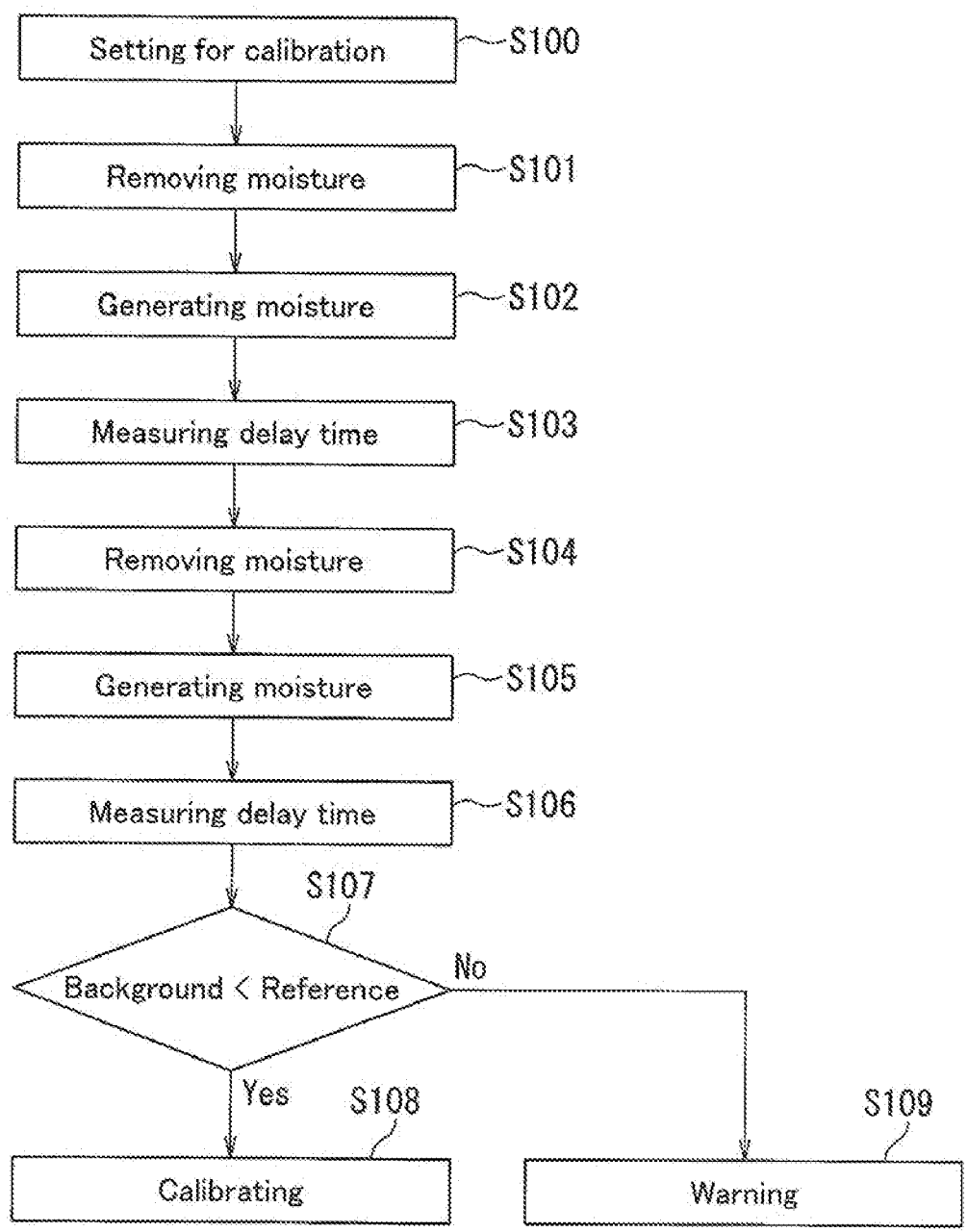
[FIG. 21]

STANDARD-MOISTURE GENERATOR, SYSTEM USING THE STANDARD-MOISTURE GENERATOR, METHOD FOR DETECTING ABNORMALITY IN STANDARD-MOISTURE AND COMPUTER PROGRAM PRODUCT FOR DETECTING THE ABNORMALITY

TECHNICAL FIELD

The present invention relates to a standard-moisture generator, a system using the standard-moisture generator, a method for detecting an abnormality in a standard-moisture and a computer program product for detecting the abnormality.

BACKGROUND ART

Measurements and controls of moistures in gaseous materials are an important schemes for the quality managements in manufacturing semiconductor devices and apparatus for light emitting displays. There are various technologies of moisture measurement using an aluminum oxide sensor, a tunable laser diode and a cavity ring down spectroscopy (CRDS). Recently, in NPL 1, a new technology called "a ball surface acoustic wave (SAW) moisture sensor" has been reported. The ball SAW moisture sensor covers a wide range of moisture levels, from a few ppbv to hundreds ppmv, and the most prominent characteristics of the ball SAW moisture sensor is quick response to a sudden variation in the moisture (refer to NPL 2).

For any methods of moisture measurement, calibration of the moisture levels, is inevitable. It is established that the calibration of a particular sensor can be traced back to an international standard (refer to NPL 3). It is also important to periodically validate the sensor accuracy against the calibrated values while the sensor is running in the field of measurement, such as factories and pipe lines (refer to NPL 4). In order to calibrate and validate the moisture sensors, the accurate generations of moisture at certain predetermined values are crucial. Various methods of moisture generation have been proposed and implemented including a diffusion tube method (refer to NPL 5), a national physical laboratory (NPL) method (refer to NPL 6) and a method using a permeation tube (refer to NPL 7).

Of the methods of moisture generation, the method using the permeation tube is suitable for facilitating the onsite validation because of its small volume. The permeation tube is made of a polymer tube with a certain diameter and a length, containing water in it. A tightly sealed cell containing the permeation tube is connected to a pipe line, so that the gas flows into and out of the cell at a regulated constant flow rate. The polymeric material is permeable to water molecules, and therefore, the cell transmits the water molecules at a constant rate when the temperature and pressure are maintained constant. The amount of moistures generated by the permeation tube are normally controlled by changing the temperature. As a result, the amount of moisture in the output gas from the cell is a sum of the original moistures in the input gas and the one generated by the permeation tube. Therefore, the output gas can be used as a standard moisture when the input gas contains a small enough amount of moisture for the validation. For using as the standard moisture, a dryer containing desiccants such as silica particles are used. Then, a lifetime of the dryer is a key issue because the dryer stops absorbing the water molecules when the dryer accumulates too much water molecules.

CITATION LIST

Non Patent Literature

[NPL 1]: N. Takeda, et al.: Int. J. Thermophys. 33, 1642 (2012).
[NPL 2]: T. Tsuji, et al.: Jpn. J. Appl. Phys. 54, 07HD13 (2015)
[NPL 3]: H. Abe, et al.: Sensors and Actuators A: Physical, 165, 230 (2011).
[NPL 4] G. McKeogh, et al.: D.16-McKeogh-1, presented at the GAS2017.
[NPL 5] H. Abe et al.: Sensors and Actuators A: Physical, 128, 202 (2006).
[NPL 6] M. Stevens et al.: Measurement Science and Technology, 3, 943 (1992).
[NPL 7] A. E. O'Keeffe, et al.: Anal. Chem., 38, 760 (1966).
[NPL 8] T. Ohmi: Microeclectron. Eng. 10, 163 (1991).
[NPL 9] T. Ohmi, et al.: J. Vac. Sci. Technol. A 14, 2505 (1996).
[NPL 10] T. Tsuji, et al.: Japanese Journal of Applied Physics, Volume 56, Number 7S1, June 2017.
[NPL 11] A. Jaulmes, et al.: J. Phys. Chem. 88, 5379 (1984).
[NPL 12] A. Jaulmes, et al.: J. Phys. Chem. 88, 5385 (1984).

SUMMARY OF INVENTION

Technical Problem

In view of the above problems, an object of the present invention is to provide a standard-moisture generator, a system using the standard-moisture generator, a method for detecting an abnormality of the standard-moisture generator and a computer program product for detecting the abnormality, which can guarantee that a dryer connecting to a cell including a permeation tube is working properly.

Solution to Problem

A first aspect of the present invention inheres in a standard-moisture generator. Here, the standard-moisture generator has (a) a flow controller configured to control a flow of a gas, (b) a dryer connected to the flow controller, configured to absorb water molecules in the gas and to generate a dry gas having a background moisture, (c) a moisture cell connected to the dryer, configured to add an object moisture to the dry gas; and a delay member connected to the moisture cell, configured to pass the dry gas with a delay time depending on a concentration of the background moisture in the dry gas.

A second aspect of the present invention inheres in a system for detecting an abnormality in a standard-moisture. The system pertaining to the second aspect of the present invention includes (a) a standard-moisture generator having, a flow controller configured to control a flow of a gas, a dryer connected to the flow controller, configured to absorb water molecules in the gas and to generate a dry gas having a background moisture, a moisture cell connected to the dryer, configured to add an object moisture to the dry gas, and a delay member connected to the moisture cell, configured to pass the dry gas with a delay time depending on a concentration of the background moisture in the dry gas, (b) a sensor unit having a ball surface-acoustic-wave sensor connected to an outlet of the delay member, configured to detect the moisture concentration in the dry gas, and (c) a processing unit having, a moisture control module configured to regulate the flow controller and the moisture cell so as to flow the dry gas with the object moisture and the background moisture into the delay member, a detection module configured to control the ball surface-acoustic-wave sensor to detect the moisture concentration in the dry gas, and a measurement module configured to calculate the delay time using the moisture concentration in the dry gas.

A third aspect of the present invention inheres in a method for detecting an abnormality in a standard-moisture, using a standard-moisture generator having a flow controller, a dryer, a moisture cell and a delay member, and a ball surface-acoustic-wave sensor. The method pertaining to the third aspect of the present invention includes (a) flowing a gas into the dryer by the flow controller so as to feed a dry gas having a background moisture, (b) removing water molecules on an inner surface of the delay member while a permeation tube in the moisture cell is cooled down to a temperature not to evaporate moisture from the permeation tube by a Peltier unit provided in the moisture cell, (c) generating an object moisture to be added to the dry gas by the moisture cell while the permeation tube is heated to a temperature to evaporate moisture by the Peltier unit, (d) passing the dry gas with the object moisture and the background moisture through the delay member, (e) measuring a delay time depending on a moisture concentration of the background moisture in the dry gas, the delay time is defined by a time between an onset of flowing the dry gas and a leading edge of a measured moisture concentration at one half of the object moisture, and (f) comparing a measured background moisture concentration to a reference.

A fourth aspect of the present invention inheres in a computer program product for detecting an abnormality in a standard-moisture, driving a computer system including a standard-moisture generator having a flow controller, a dryer, a moisture cell and a delay member, and a ball surface-acoustic-wave sensor. The computer program product pertaining to the fourth aspect of the present invention includes (a) instructions to flow a gas into the dryer by the flow controller so as to feed a dry gas having a background moisture, (b) instructions to remove water molecules on an inner surface of the delay member while a permeation tube in the moisture cell is cooled down to a temperature not to evaporate moisture from the permeation tube by a Peltier unit provided in the moisture cell, (c) instructions to generate an object moisture to be added to the dry gas by the moisture cell while the permeation tube is heated to a temperature to evaporate moisture by the Peltier unit, (d) instructions to pass the dry gas with the object moisture and the background moisture through the delay member, (e) instructions to measure a delay time depending on a moisture concentration of the background moisture in the dry gas, the delay time is defined by a time between an onset of flowing the dry gas and a leading edge of a measured moisture concentration at one half of the object moisture, and (f) instructions to compare a measured background moisture concentration to a reference.

Advantageous Effects of Invention

According to the present invention, it is possible to provide the standard-moisture generator, the system using the standard-moisture generator, the method for detecting an abnormality of the standard-moisture generator and the computer program product for detecting the abnormality, which can guarantee that the dryer connecting to a cell including the permeation tube is working properly.

BRIEF DESCRIPTION OF DRAWINGS

FIG. 1 is a block diagram illustrating an example of a detection system for abnormality in a standard-moisture according to an embodiment of the present invention;

FIG. 2 is a schematic cross sectional view illustrating an example of a sensor unit using a ball SAW sensor according to the embodiment of the present invention;

FIG. 3 is a schematic view illustrating an example of the ball SAW sensor used in the detection system for abnormality according to the embodiment of the present invention;

FIG. 4 is a schematic view illustrating an example of the standard-moisture generator according to the embodiment of the present invention;

FIG. 5 is a schematic view illustrating an example of a pipe in which an inert gas containing moisture flows through;

FIG. 6 is a diagram illustrating an example of calculated time-dependence of moisture at the outlet of the pipes;

FIG. 7 is a diagram illustrating an example of a moisture generator for simulation;

FIG. 8 is a diagram illustrating examples of calculated time-dependences of moisture at the outlet of the EP tube;

FIG. 9 is a diagram illustrating other examples of calculated time-dependences of moisture at the outlet of the EP tube;

FIG. 10 is a diagram illustrating an example of an experimental setup of a moisture generator;

FIG. 11 is a diagram illustrating examples of measured signals of the ball SAW sensor for background moisture of 0.05 ppmv;

FIG. 12 is a diagram illustrating examples of measured signals of the ball SAW sensor for background moisture of 0.2 ppmv;

FIG. 13 is a diagram illustrating examples of measured signals of the ball SAW sensor for background moisture of 0.5 ppmv;

FIG. 14 is a diagram illustrating examples of measured signals of the ball SAW sensor for background moisture of 1 ppmv;

FIG. 15 is a diagram illustrating other examples of measured signals of the ball SAW sensor for background moisture of 0.06 ppmv;

FIG. 16 is a diagram illustrating other examples of measured signals of the ball SAW sensor for background moisture of 0.2 ppmv;

FIG. 17 is a diagram illustrating other examples of measured signals of the ball SAW sensor for background moisture 0.5 ppmv;

FIG. 18 is a diagram illustrating an example of theoretical and experimental delay time plotted as a function of background moisture;

FIG. 19 is a diagram illustrating another example of theoretical and experimental delay time plotted as a function of background moisture;

FIG. 20 is a schematic view illustrating an example of the standard-moisture generator for validation of a moisture sensor according to the embodiment of the present invention; and FIG. 21 is a flow chart illustrating an example of a validation method of a moisture sensor according to the embodiment of the present invention.

DESCRIPTION OF EMBODIMENTS

Embodiments of the present invention will be described below with reference to the drawings. In the descriptions of the following drawings, the same or similar reference numerals are assigned to the same or similar portions. However, the drawings are diagrammatic, and attention should be paid to a fact that the relations between thicknesses and plan view dimensions, the configuration of the apparatus and the like differ from the actual data. Thus, the specific thicknesses and dimensions should be judged by considering the following descriptions. Also, even between the mutual drawings, the portions in which the relations and rates between the mutual dimensions are different are naturally included. Also, the embodiments as described below exemplify the apparatuses and methods for embodying the technical ideas of the present invention, and in the technical ideas of the present invention, the materials, shapes, structures, arrangements and the like of configuration parts are not limited to the followings.

In the following description, $\Delta$ represents Greek alphabet capital letter, $\xi$, $\pi$ and $\tau$ represent Greek alphabet lower-case letters, and $\partial$ represents partial derivative symbol expressed by "curved d" or "rounded d", respectively. And, the "horizontal" direction or the "vertical" direction is simply assigned for convenience of explanation and does not limit the technical spirit of the present invention. Therefore, for example, when the plane of paper is rotated 90 degrees, the "horizontal" direction is changed to the "vertical" direction and the "vertical" direction is changed to the "horizontal" direction. When the plane of paper is rotated 180 degrees, the "left" side is changed to the "right" side and the "right" side is changed to the "left" side. Therefore, various changes can be added to the technical ideas of the present invention, within the technical scope prescribed by claims.

System Configuration

As illustrated in FIG. 1, a detection system for abnormality in a standard-moisture pertaining to an embodiment of the present invention includes a sensor unit 1, a moisture generator 5, a gas supply unit 3 and a processing unit 4. The sensor unit 1 has, as illustrated in FIG. 2, a ball SAW sensor 2 embedded in a tubular sensor cell 31, which is fixed on a plate-shaped adapter 14 disposed on a block-shaped holder 11. It is noted that FIG. 2 exemplifies the sensor unit 1 having the ball SAW sensor 2, it is not limited and other designs or configurations are also applicable. For example, the ball SAW sensor 2 embedded in a tubular sensor cell 31, which is fixed on a plate-shaped adapter 14 disposed on a block-shaped holder 11. As the ball SAW sensor 2 has spherical shape, with a tubular configuration, the inner structure of the sensor cell 31 has a concave configuration for mounting a lower portion of the ball SAW sensor 2. An electrode-holder base 32 is fixed on the sensor cell 31, such that the bottom of the electrode-holder base 32 is inserted in an inner wall of a window, which is vertically cut at the top wall of the tubular sensor cell 31. An opening of a canal, which penetrates vertically through the bottom of the electrode-holder base 32, partially covers an upper portion of the ball SAW sensor 2. Furthermore, the electrode-holder base 32 is capped by a sensor-cell cap 33.

The ball SAW sensor 2 is connected to a rod-shaped external electrode 35 through a contact pin 35a along a vertical direction via the canal at the bottom of the electrode-holder base 32. The external electrode 35 is held in a hollow space of a vertically aligned cylindrical electrode holder 34, the bottom of which is inserted in an inner portion of the sensor-cell cap 33. A sensing gas containing in a background gas, for example, a humid gas, is introduced into the sensor cell 31 through a horizontally aligned tubing 36 with a gas flow rate v, so that the humid gas can touch the surface of the ball SAW sensor 2. The gas flow rate v is typically 0.1 L/min to 1 L/min.

As illustrated in FIG. 3, the ball SAW sensor 2 may have a sensor electrode 22 and a sensitive film 23 arranged in predetermined areas on the surface of a homogeneous piezoelectric ball 20. As a three-dimensional base body, the piezoelectric ball 20 provides a homogeneous material sphere, on which a circular orbital band for propagating a SAW can be defined. The sensor electrode 22 generates a collimated beam 21 of the SAW, which propagates repeatedly through the circular orbital path defined on the piezoelectric ball 20 while passing through the sensitive film 23 deposited on the orbital path. The sensitive film 23 can be formed on almost the entire surface of the orbital band, which defines the orbital path on the three-dimensional base body. Because the sensitive film 21 is configured to react with specific gas molecules, the sensitive film 21 adsorbs molecules of water vapor in the sensing gas-to-be-measured.

For the piezoelectric ball 20, a crystal sphere, such as quartz, langasite ($La_3Ga_5SiO_{14}$), lithium niobate ($LiNbO_3$), lithium tantalate ($LiTaO_3$), piezoelectric ceramics (PZT), bismuth germanium oxide ($Bi_{12}GeO_{20}$) and the like, may be used. For the sensitive film 23, a silica ($SiO_x$) film and the like may be used. The sensor electrode 22 may be deposited in an opening of the sensitive film 23, the opening exposes a part of the surface of the piezoelectric ball 20, in a configuration such that the opening is formed on a part of the equator of the homogeneous piezoelectric ball 20. For the sensor electrode 22, an interdigital electrode (IDT) using a chromium (Cr) film and the like may be used as an electroacoustic transducer. In the case of a sphere of single crystal such as the homogeneous piezoelectric ball 20, a SAW orbiting route is limited to a specific orbital band having a constant width, depending on type of crystal material. The width of the orbital band may be increased or decreased depending on anisotropy of the crystal.

There are no diffraction losses during roundtrips around the piezoelectric ball 20, and only propagation loss due to material attenuation. The collimated beam 21 is scheduled to propagate many turns passing through the sensitive film 23, which is configured to adsorb water molecules. Because the adsorbed water molecules change the propagation characteristic of the SAW, the changes due to adsorbed water molecules on the sensitive film 23 can be integrated every turn through the multiple roundtrips. Thus, even though the sensitive film 23 may be so thin as to adsorb the small amount of the water vapor, measurement accuracy of water concentration may be increased.

For example, the ball SAW sensor 2 may be fabricated as described below. A pattern of an IDT of about 150 nanometers thick Cr film is deposited on a surface of a quartz ball having a diameter of 3.3 millimeters. The IDT has a pair of bus bars, and a plurality of electrode fingers extending from the bas bars, respectively. The electrode fingers overlap each other with a cross width Wc, and each electrode finger has a width Wf and a periodicity P. The cross width Wc, the width Wf and the periodicity P are designed as 364 micrometers, 6.51 micrometers and 10.0 micrometers, respectively, for the natural collimation of 80 MHz SAW.

The IDT on the quartz ball having 3.3 millimeters diameter can generate 80 MHz SAW. Then a silica film is synthesized by using a sol-gel method and coated on the surface of the quartz ball as follows: 3.47 grams of tetraethoxysilane (TEOS), 0.75 grams of isopropanol (IPA), and 1.50 grams of 0.1N hydrochloric acid (HCl) are mixed and stirred by sonication (27, 45, 100 kHz, 60 minutes). TEOS is polymerized by hydrolysis and resulted in $SiO_x$. After sonication, the mixture is diluted with IPA and 0.5 mass % $SiO_x$ solution is obtained. The surface of propagation route of SAW is coated with the $SiO_x$ solution using a spin coating. Condition of the spin coating is 3000 rpm for 20 seconds. The thickness of $SiO_x$ film is confirmed as 1029 nanometers from measurement using interference microscope.

It should be noted that the method for fabricating the ball SAW sensor 2 has been described above. However, a material and a fabrication method of the sensor electrode 22 and the sensitive film 23 are not limited, and other materials and other fabrication methods may also be adopted.

An RF voltage is applied to the sensor electrode 22 via an electrode pad (not illustrated) arranged around the north-pole, which is a top of the piezoelectric ball 20 in FIG. 3, using the contact pin 35*a* attached on the bottom of the external electrode 35. Another electrode pad (not illustrated) arranged around the south-pole, which is a bottom of the piezoelectric ball 20 in FIG. 3, is in contact with the grounded sensor cell 31.

As illustrated in FIG. 2, the temperature controller 16 is connected to a Peltier element 12, which is held in a lower portion of the holder 11 at a position just below the ball SAW sensor 2, and a thermistor 13 is inserted in the holder 11 at a side position of the holder 11. Furthermore, the temperature controller 16 is connected to the thermistor 13. The Peltier element 12 is used for heating and cooling the ball SAW sensor 2 in the sensor cell 31 through the adapter 14. The thermistor 13 is used for detecting a monitoring temperature of the holder 11. The temperature controller 16 controls the Peltier element 12 by using the monitoring temperature. As illustrated in FIG. 2, the thermistor 13 cannot be directly inserted into the sensor cell 31 to prevent leakage of gases through the sensor cell 31. Note that, although the thermistor 13 is used for detecting the monitoring temperature in the first embodiment, but other thermometers, such as a thermocouple and the like, may be used. It is noted that the temperature control of the ball SAW sensor 2 is a method to accurately measure trace moisture stably over a long term, and it is not absolutely necessary to execute temperature modulation by the Peltier element 12.

The gas supply unit 3 illustrated in FIG. 1 may supply a gas to the standard-moisture generator 5 for a calibration and validation of a moisture sensor. The gas supply unit 3 has a gas source of an inert gas, such as a nitrogen ($N_2$) gas, an argon (Ar) gas and the like, and is connected to the inlet 58 of the standard-moisture generator 5. And the gas supplied from the gas supply unit 1 contains a residual moisture.

The standard-moisture generator 5, as illustrated in FIG. 4, includes flow controllers 50, 51, an auto pressure regulator (APR) 52, a switching valve 53, a dryer 54, a moisture cell (55, 56) and a delay member 57. A gas supplied from the gas supply unit 3 illustrated in FIG. 1, may be fed to the flow controllers 50, 51 and the APR 52 through an inlet 58 of the standard-moisture generator 5.

The flow controllers 50, 51 may control a flow rate of the supplied gas. For the flow controllers 50, 51, a mass flow controller may be used. The APR 52 may regulate a pressure in an exhaust line connected to an exhaust 60 of the standard-moisture generator 5. The dryer 54 may remove water molecules in the supplied gas by absorption to feed a dry gas having a background moisture. For the dryer 54, a desiccant, such as silica gel, molecular sieve and the like may be used. The moisture cell (55, 56) has a permeation tube 55 and a Peltier unit 56. The permeation tube 55 may generate moisture having a predetermined concentration with a temperature control by the Peltier unit 56, so as to add an object moisture to the supplied gas. The delay member 57 may pass the object moisture in the dry gas with a delay time depending on a background moisture concentration in the supplied gas. For the delay member 57, a metal tube made of stainless steel in which an inner surface is treated by electropolishing (EP) or electrochemical-buffing (ECB) may be used so as to control surface density of adsorption site. The metal tube may preferably have a length of 5 centimeters or more and 30 centimeters or less. Further, the delay member 57 may include a metal-mesh filter made of stainless steel having a surface treated by EP or ECB, not only to remove particles in the dry gas, but also to maintain surface density of adsorption site at an appropriate level.

As illustrated in FIG. 4, the switching valve 53 can switch between a normal mode and a calibration mode. In the calibration mode illustrated by a solid line in FIG. 4, the switching valve 53 connects: the flow controller 50 to the exhaust 60; and the flow controller 51 to the inlet of the dryer 54, the outlet of the dryer 54 to the inlet of the moisture cell (55, 56), the outlet of the moisture cell (55, 56) to the inlet of the delay member 57, and the outlet of the delay member 57 to the outlet 59 of the standard-moisture generator 5. In the calibration, the sensor unit 1 is connected to the outlet 59 of the standard-moisture generator 5. Therefore, in the calibration mode, the gas supplied through the flow controller 51 to the dryer 54, passes the permeation tube 55 and the delay member 57, and feeds to the sensor unit 1 through the outlet 59 of the standard-moisture generator 5. The APR 52 may regulate the input pressure of the flow controllers 50, 51 so as to stably control flow rates of the flow controllers 50, 51.

In the normal mode illustrated by a dotted line in FIG. 4, the switching valve 53 connects:

(a) the flow controller 50 to the outlet 59 of the standard-moisture generator 5;

(b) the flow controller 51 to the inlet of the moisture cell (55, 56);

(c) the outlet of the moisture cell (55, 56) to the exhaust 60;

(d) the inlet of the dryer 54 to the inlet of the delay member 57; and (e) the outlet of the dryer 54 to the outlet of the delay member 57.

In the normal mode, the gas passing through the flow controller 50 is fed to the outlet 59 of the standard-moisture generator 5, and the gas passing through the flow controller 51 and the permeation tube 55 is fed to the exhaust 60 of the standard-moisture generator 5.

The processing unit 4, as illustrated in FIG. 1, includes a moisture module 41, a detection module 42, a measurement module 43 and a storage module 44. The moisture control module 41 sends instructions to the gas supply unit 3 and the standard-moisture generator 5 for regulating the flow controller 51 so as to flow the dry gas having a background moisture from the dryer 54 to the outlet 59 where the sensor unit 1 is connected. The moisture control module 41 controls to add an object moisture, using the permeation tube 55 with heating the Peltier unit 56, and to pass the dry gas with the object moisture and the background moisture through the delay member 57 with a delay time. The delay time depends on a moisture concentration in the dry gas.

The detection module 42 sends instructions to the sensor unit 1 for transmitting an exciting burst signal to the sensor electrode 22 of the ball SAW sensor 2 and the sensor electrode 22 can excite the collimated beam 21 of a SAW propagating around the piezoelectric ball 20 illustrated in FIG. 3. Furthermore, the detection module 42 sends instructions to the sensor unit 1 for receiving returned burst signals of the collimated beam 21 through the sensor electrode 22 after the collimated beam 21 has propagated a predetermined number of turns around the piezoelectric ball 20 illustrated in FIG. 3. And, the detection module 42 transmits waveform data of the returned burst signals to the measurement module 43. The measurement module 43 calculates the moisture concentration in the dry gas by using the waveform data of the returned burst signals, and measures a delay time using time-dependence of the moisture concentration in the dry gas. And further, the measurement module 43 compares the delay time to a reference and warns of abnormality in the standard-moisture generator 5 when the delay time is larger than the reference.

The storage module 44 of the processing unit 4 stores a program for driving the processing unit 4 to implement processing of the waveform data for calculating the delay time. Also, the storage module 44 stores the data of references of delay times for various moisture concentrations, and data obtained during the calculation and analysis of the gas during the operation of the processing unit 4.

The processing unit 4 may be part of central processing unit (CPU) of a general purpose computer system, such as a personal computer (PC) and the like. The processing unit 4 may include an arithmetic logic unit (ALU) that performs arithmetic and logic operations, a plurality of registers that supply operands to the ALU and store the results of ALU operations, and a control unit that orchestrates the fetching (from memory) and execution of instructions by directing the coordinated operations of the ALU. The moisture control module 41, the detection module 42, and the measurement module 43 implementing the ALU may be discrete hardware resources, such as logical circuit blocks or the electronic circuitry merged in a single integrated circuit (IC) chip, or alternatively, may be provided by virtually equivalent logical functions achieved by software, using the CPU of the general purpose computer system.

In addition, the program for the processing unit 4 for detecting the abnormality of the standard-moisture generator is not limited to being stored in the storage module 44 which is installed in the processing unit 4. For example, the program may be stored in an external memory. Moreover, the program may be stored in a computer readable medium. By reading the computer readable medium in the storage module 44 of the computer system, which includes the processing unit 4, the processing unit 4 executes coordinated operations for detecting the abnormality of the standard-moisture generator, in accordance with a sequence of instructions recited in the program. Here, the "computer readable medium" refers to a recording medium or a storage medium, such as an external memory unit of a computer, a semiconductor memory, a magnetic disk, an optical disk, a magneto optical disk, and a magnetic tape, on which the program can be recorded. With the program for the processing unit 4 for driving the standard-moisture generator and the method for detecting an abnormality of the standard-moisture generator according to the embodiment of the present invention, validation of a ball SAW sensor used for monitoring trace-moisture may be easily achieved.

Analysis of Moisture in a Gas Flowing Through a Pipe

First, behavior of water molecules in a gas flowing through a pipe, or tube, will be described. The water molecules are readily adsorbed to an inner surface of a pipe, a cylinder or a chamber when a gas containing moisture flows through the pipe, the cylinder or the chamber. The water molecules are one of the contaminants seriously affecting the quality of products processed using the pipe, the cylinder or the chamber (refer to NPL 8). It has been reported that a smaller amount of water molecule is adsorbed on a smoother inner surface of a metal pipe (refer to NPL 9). Recently, in NPL 10, the present authors have reported that a quantitative analysis of correlation between the degree of surface treatment, such as electrochemical buffing (ECB) and electropolishing (EP), and the amount of water adsorption, may be possible when a ball SAW sensor monitors the time-dependence of moisture in a gas passing through a metal pipe of 10 centimeters long. Such analysis reported in NPL 10 has been made possible because the ball SAW sensor has a quick response time within a few seconds. In the following, we propose a theoretical model to describe the time-dependence of the moisture in an infinitesimally small volume of an inert gas that is flowing through a pipe.

Theoretical Analysis

There have been theoretical and experimental studies on the behavior of molecules contained in a carrier gas passing through a capillary column in a gas chromatograph (refer to NPLs 11, 12). Although interaction of those molecules with the inner surface of the capillary column is basically a linear function of the number of molecules, the secondary nonlinear effect is taken into account for the detail analysis of deviation from the linear model. Such analysis correctly reflected the most prominent feature of gas chromatography in that the retention time is independent of the number of molecules of interest. In contrast, the adsorption to and desorption from the metal surface of water molecules seem to be fundamentally nonlinear function of the moisture as described in the following. A detail of the model will be found in a following SUPPLIMENTARY EXPLANATION, which is recited in latter part of the present Specification.

Let us assume an inert gas is flowing at constant flow rate $f$ [m$^{-3}$ s$^{-1}$] through a pipe with a length L [meters] and an inner diameter d [meters], as illustrated in FIG. 5. The surface density of adsorption sites is s [mol m$^{-2}$], and an adsorption ratio to the sites, or how much ratio of the adsorption sites is occupied with water molecules, is r. The normalized moisture is W, that is $$W = (wL^3)/(sL^2) \tag{1}$$

where w is the moisture measured in [mol m$^{-3}$]. A set of normalized dimensionless equations is given as follows, where $g = (4L)/d$, and "a" and "b" are only adjustable parameters.

$$\partial r/\partial \tau = -a \cdot r + b \cdot (1-r) \cdot W, \tag{2}$$

$$\partial W/\partial \tau + \partial W/\partial \xi = g \cdot a \cdot r - g \cdot b \cdot (1-r) \cdot W, \tag{3}$$

$\tau$ and $\xi$ are normalized time and space coordinate, respectively, defined by $$\tau = 4t \cdot f/(\pi L \cdot d^2) \tag{4}$$

$$\xi = x/L, \tag{5}$$

where t and x are time and space coordinates measured in [seconds] and [meters], respectively. A computer program has been developed to numerically solve the equations.

To simulate the experiments in NPL 10, we set the values of parameters as follows.
f: 0.1 [litter/minute]
L: 10 [centimeters]
d: 4.35 [millimeters]

$w_0$: 1 ppbV
$w_1$: 1 ppmV.

Assuming a=1 and b=1 for simplicity and adjusting the surface density s, we obtain the time-dependence of moisture measured at the outlet of the pipe for an ECB tube and an EP tube, respectively, as shown in FIG. 6. The leading edges for the ECB tube and the EP tube reasonably match the experimental values of 15 seconds and 40 seconds, respectively, in NPL 10.

Now we simulate the behavior of moisture in a configuration illustrated in FIG. 7, where an inert gas with unknown moisture passes through a dryer 54 and then flows into a moisture cell including a permeation tube 55. The moisture cell further includes a bypass 71 and switching valves 70a, 70b. The output of the permeation tube 55 goes into an EP tube 57a with L=16 centimeters. We assume that the temperature of the permeation tube 55 is controlled so as to generate 1 ppmv and 5 ppmv moisture, respectively. Then, we solve the equations for the moisture in the EP tube 57a with a set of different initial conditions which simulates the uncontrollable variation of the moisture coming out of the dryer 54. FIG. 8 shows the calculated time-dependence of moisture at the outlet of the EP tube 57a for the different set of initial conditions at the inlet of the EP tube 57a. We simulates the situations where the output of the dryer 54 contains the moisture of 0.05 ppmv, 0.2 ppmv, 0.5 ppmv and 1 ppmv, respectively, and then the permeation tube 55 adds 1 ppmV moisture. It is confirmed that capability of the dryer 55 can be evaluated by measuring the delay time between the onset of gas flow and the leading edge of the moisture change at the outlet of the EP tube 57a. FIG. 9 illustrates similar analysis where the output of the dryer 54 contains the moisture of 0.06 ppmv, 0.2 ppmv and 0.5 ppmv, respectively, and then the permeation tube 55 adds 5 ppmv moisture. It is still valid that the capability of the dryer 54 can be evaluated by measuring the delay time between the onset of gas flow and the leading edge of the moisture change at the outlet of the EP tube 57a, though the time difference is smaller for the larger moisture.

Experiment

FIG. 10 illustrates an experimental setup to validate the theoretical prediction. The nitrogen ($N_2$) gas having controlled values of moisture is fed into a moisture cell (55, 56) including the permeation tube 55 and the Peltier unit 56, through the dryer 54, a flow controller 80 and valves 88a, 88b, 88c. Also, the $N_2$ gas is fed to the outlet of the permeation tube 55, through a diffusion tube 85, a flow controller 82, 83 and valves 89a, 89b, so as to add a background moisture in the gas flowing to the delay member 57. And the gas goes into a delay member which is 10 centimeters long EP tube, through a switching valve 84. The gas coming out of the delay member 57 flows through a metal-mesh filter for removal of particles before the gas reaches the measurement cell of the ball SAW sensor. In the numerical calculation in the previous section, the effect of the metal-mesh filter to the delay has been taken into account by assuming 16 centimeters long EP tube. In addition, the experimental setup further includes a cavity ring-down spectroscopy (CRDS) cell 87 as a comparison sensor against the ball SAW sensor 2, a flow controller 81 with valves 88d, 88e for purging the CRDS cell 87 in "on" state and the delay member 57 in "off" state, and the APR 86 for controlling the pressure of the $N_2$ gas.

FIGS. 11 to 14 illustrate measured signals of the ball SAW sensor 2 of FIG. 3, for four different conditions as indicated with:

(the background moisture from the diffusion tube 85)+
(the standard-moisture from the permeation tube 55):
0.05 ppmv+1 ppmv,
0.2 ppmv+1 ppmv,
0.5 ppmv+1 ppmv and
1 ppmv+1 ppmv, respectively. The vertical axis is a moisture concentration by a normalized value of the moisture by the ball SAW sensor 2 because the absolute value is not calibrated yet. The experiment has been repeated for four times with each condition. FIGS. 15 to 17 illustrate measured signals for:

(the background moisture from the diffusion tube 85)+
(the standard-moisture from the permeation tube 55):
0.06 ppmv+5 ppmv,
0.2 ppmv+5 ppmv and
0.5 ppmv+5 ppmv, respectively. It should be noted that the delay time between the onset of flowing the target gas to the delay member 57 and the leading edge of the change in the moisture concentration, depends on the background moisture as predicted by the theoretical simulation, as illustrated in FIGS. 11 to 17. In addition, as illustrated in FIGS. 11 to 17, the leading edge is defined by a measured moisture concentration is one half of the standard-moisture. More quantitatively, the theoretical and experimental delay times are summarized and plotted in FIGS. 18 and 19. As illustrated in FIGS. 18 and 19, the theoretical and experimental values do not exactly match but the trend is reproduced correctly that the smaller the background moisture the larger the delay time.

As mentioned above, the metal tube having the inner surface treated by electropolishing or electrochemical-buffing, as the delay member 57 illustrated in FIG. 4, and the ball SAW sensor 2 of FIG. 3, having a quick response time as the moisture sensor, are used in the standard-moisture generator according to the embodiment. As illustrated in the experimental data of FIG. 18, it is understood that the background moisture of 0.5 ppmv added to the 5 ppmv standard moisture gives rise to the time delay of −50%. Also, as illustrated in FIG. 19, the background moisture of 0.1 ppmv added to the 1 ppmv standard moisture gives rise to the time delay of −27%. Therefore, it is possible to conclude that by measuring the delay time using the ball SAW sensor 2, the uncontrollable background moisture at less than 10% can be easily distinguished. This is a unique way of guaranteeing the accuracy of the standard moisture for the validation of ball SAW sensors. Thus, it is possible to guarantee that the dryer 54 connecting to the moisture cell (55, 56) including the permeation tube 55 is working properly. Further, validation of the ball SAW sensor 2 used for monitoring trace-moisture may be easily achieved in a field of measurement in factories, pipe lines and the like.

In addition, in the calibration mode illustrated in FIG. 20, the delay member 57 may purge the inner surface having adsorbed water molecules. For example, the Peltier unit 56 is used to cool the permeation tube 55 at a temperature less than 0° C., more preferably less than −10° C., during flowing the $N_2$ gas into the delay member 57. Since the water molecules are not generated from the permeation tube 55 in the low temperature, then the inner surface of the delay member 57 can be purged. As stated above, by using the standard-moisture generator and the method for detecting an abnormality of the standard-moisture generator according to the embodiment, validation of a ball SAW sensor used for monitoring trace-moisture can be easily achieved. Therefore the standard-moisture generator and the method for detecting an abnormality of the standard-moisture generator according to the embodiment can be used in a field of measurement in factories, pipe lines and the like.

Supplimentary Explanation

Let us assume that an ideal gas containing water molecules flows through a pipe with a length L [m] and an inner diameter d [m] at a constant flow rate f [m$^3$ s$^{-1}$]. We assume that the flow velocity is uniform over the entire cross-section of the pipe for simplicity. Then, the flow velocity v is $$v=4f/(\pi d^2) \quad (A1)$$

We propose that there are microscopic sites on the inner surface of the metal pipe with a surface density s [mol m$^{-2}$] where water molecules can be adsorbed. The water molecules attach to and detach from these sites at each instant, and on average there are sr sites with water molecules adsorbed per unit area, where r is an adsorption ratio.

In the experiment recited in NPL 10, the nitrogen gas with a constant moisture $w_0$ [mol m$^{-3}$] flows into the pipe from the inlet (x=0). The moisture at the outlet (x=L) eventually becomes equal to that at the inlet after a sufficiently long time. Then, the moisture of the gas flowing into the inlet is suddenly changed to another constant value $w_1$ [mol m$^{-3}$] at time t=0, and the time dependence of the moisture at the outlet (w(t, x=L)) is monitored.

The amount of water molecules that detach from the unit area of the inner surface and enter into the carrier gas is proportional to the amount of adsorbed water molecules on the unit area, sr. Thus, introducing a coefficient $k_d$, it is $srk_d$. On the other hand, the amount of water molecules adsorbed on the unit area of the inner surface is proportional to the product of the number of vacant sites, s(1−r), and the number of water molecules in the carrier gas or moisture, w. Thus, it is, s(1−r) $k_a$w, where $k_a$ is a coefficient.

Now let us take a volume with a length Δx at a position x=$x_0$ along the length of the pipe. The amount of water molecules contained in the volume increases due to the incoming flow from the upstream and decreases due to the outgoing flow to the downstream, and the net increase due to the flow during a time interval Δx is their difference, $$-(\partial w/\partial x)\cdot v\cdot (d/2)^2\cdot \pi\cdot \Delta x\cdot \Delta t. \quad (A2)$$

In this time interval, a part of the water molecules in the gas flow are adsorbed on the metal surface and a part of the water molecules on the surface detach from the surface, and the net amount of adsorbed molecules is, $$[sk_d r(t,x)-sk_a(1-r(t,x))w(t,x)]\cdot \pi\cdot d\cdot \Delta x\cdot \Delta t. \quad (A3)$$

The diffusion of water molecules may occur when there is a difference of moisture along the length of the pipe, but here we ignore it assuming its effect is smaller than that of the equations Eq. (A2) and Eq. (A3). We can take it into account if necessary by introducing a diffusion term, $$D(\partial^2 w/\partial x^2)\cdot (d/2)^2\cdot \pi\cdot \Delta x\cdot \Delta t. \quad (A4)$$

Taking the equations Eq. (A2) and Eq. (A3) into a dimensionless form, we have $$\partial r/\partial \tau=-a\cdot r+b\cdot (1-r)\cdot W, \quad (A5)$$

$$\partial W/\partial \tau+\partial W/\partial \xi=g\cdot a\cdot r-g\cdot b\cdot (1-r)\cdot W, \quad (A6)$$

where $$\tau=(tv)/L \quad (A7)$$

$$\xi=x/L \quad (A8)$$

$$W=(wL^3)/(sL^2) \quad (A9)$$

$$a=(Lk_d)/v \quad (A10)$$

$$b=(sk_a)/v \quad (A11)$$

$$g=(4L)/d. \quad (A12)$$

In the equilibrium $$\partial W/\partial \tau=\partial r/\partial \tau=0, \quad (A13)$$

therefore, from Eqs. (A5) and (A6), $$W=\text{constant}=W_0, \quad (A14)$$

and $$r=r_0=1/\{1+(a/b)(1/W_0)\}. \quad (A15)$$

and

Eq. (A15) means that the adsorption rate r reaches $r_0$ regardless of the position along the length of the pipe x when the gas with a constant moisture, W=constant=$W_0$, flows through the pipe for a long time. Furthermore, $$r_0 \to 0 \text{ when } (W_0 \to 0), \quad (A16)$$

$$r_0 \to 1 \text{ when}(W_0 \to \infty), \quad (A17)$$

which is obvious.

We can obtain the temporal evolution of the system by solving the Eqs. (A5) and (A6) under the boundary conditions, $$r(\tau=0,\xi)=r_0, \text{ for } (0\leq \xi \leq 1) \quad (A18)$$

$$W(\tau,\xi=0)=W_1, \text{ for } (0<\tau). \quad (A19)$$

We numerically solve the equations with the values of parameters taken from the experiments (refer to NPL 10), but the coefficients $k_d$ and $k_a$ are arbitrary assumed such that a~1 and a~b. This is equivalent to the assumption that the contribution of adsorption and desorption is in the same order in Eq. (A5).

Detection Method of Abnormality

A detection method of an abnormality in the standard-moisture generator according to the embodiment of the present invention will be described with reference to the flowchart illustrated in FIG. 21. In the detection method of an abnormality according to the embodiment, a reference of the background moisture for determine the abnormality of the standard-moisture generator 5 is set to 0.1 ppmv, for example. First, the gas piping of the target gas, for example the $N_2$ gas, from the gas supply unit 3 illustrated in FIG. 1 is connected to the inlet 58 of the standard-moisture generator 5 illustrated in FIG. 20. Also, the ball SAW sensor 2 of the sensor unit 1 is connected to the outlet 59 of the standard-moisture generator 5. the standard-moisture generator 5 and the sensor unit 1 are turned on. And, the flow controller 50 is turned on and the flow controller 51 is turned off. The switching valve 53 is set to the normal mode as illustrated in FIG. 4, so as to flow the target gas to the outlet 59.

In step S100, the switching valve 53 turns to the calibration mode as illustrated in FIG. 20, and then, the flow controller 50 is turned off and the flow controller 51 is turned on so as to flow the gas into the dryer 54 through the flow controller 51 so as to feed a dry gas having a background moisture to the permeation tube 55. Then, in step S101, the permeation tube 55 is cooling to not below 0° C. by the Peltier unit 56 to a temperature not to evaporate moisture from the permeation tube 55. Thus, water molecules adsorbed on the inner surface of the delay member 57 are removed by desorption during flowing the target gas.

Next, in step S102, temperature of the Peltier unit 56 is set to a prescribed temperature, for example, 30° C., so as to evaporate an object moisture having a predetermined concentration, for example, moisture of 5 ppmv, from the permeation tube 55. In step S103, the dry gas with the object moisture and the background moisture is passed through the delay member 57 so as to adsorb the water molecules on the inner surface of the delay member 57. During passing the dry gas, the moisture concentration is detected by the ball SAW sensor 2 so as to measure a first delay time depending on a moisture concentration of the background moisture in the dry gas. A first measured concentration of the background moisture is determined by the first delay time using the correlation between the delay time and the background concentration illustrated in FIG. 18. Here, the delay time is defined by a time between an onset of flowing the dry gas and a leading edge of a measured moisture concentration at one half of the object moisture.

In step S104, the permeation tube 55 is cooling to not below 0° C. by the Peltier unit 56 to a temperature not to evaporate moisture from the permeation tube 55. Thus, water molecules adsorbed on the inner surface of the delay member 57 in the former calibration process are removed by desorption during flowing the target gas.

In step S105, temperature of the Peltier unit 56 is set to a prescribed temperature so as to evaporate other object moisture having a predetermined concentration, for example, moisture of 1 ppmv, from the permeation tube 55. In step S106, the dry gas with the other object moisture and the background moisture is passed through the delay member 57 so as to adsorb the water molecules on the inner surface of the delay member 57. During passing the dry gas, the moisture concentration is detected by the ball SAW sensor 2 so as to measure a second delay time depending on a moisture concentration of the background moisture in the dry gas. A second measured concentration of the background moisture is determined by the second delay time using the correlation between the delay time and the background concentration illustrated in FIG. 19.

In step S107, the first and second measured concentrations of the background moisture are compared to the reference, respectively. When the first and second measured concentrations are less than the reference, in step S108, it is determined that the dryer 54 of the standard-moisture generator 5 is operating normally, and validation of the ball SAW sensor 2 may be executed. When the first and second measured concentrations are not less than the reference, in step S109, it is determined that the dryer 54 of the standard-moisture generator 5 is abnormal, and a warning is issued.

In the detection method of an abnormality in the standard-moisture generator according to the embodiment of the present, the delay time is measured by the ball SAW sensor 2. Therefore, it is possible to guarantee that a dryer connecting to a cell including a permeation tube is working properly. Further, validation of the ball SAW sensor 2 used for monitoring trace-moisture may be easily achieved in a field of measurement in factories, pipe lines and the like.

In the detection method of an abnormality in the standard-moisture generator according to the embodiment of the present, the delay time measurement is repeated twice. However, the delay time measurement is not limited twice, and the delay time measurement may be once, or three or more times.

Other Embodiments

While the present invention has been described above by reference to the embodiment, it should be understood that the present invention is not intended to be limited to the descriptions of the specification and the drawings implementing part of this disclosure. Various alternative embodiments, examples, and technical applications will be apparent to those skilled in the art according to this disclosure. It should be noted that the present invention includes various embodiments which are not disclosed herein. Therefore, the scope of the present invention is defined only by the present invention specifying matters according to the claims reasonably derived from the description heretofore.

REFERENCE SIGNS LIST

1 sensor unit
2 ball SAW sensor
3 gas supply unit
4 processing unit
11 holder
12 Peltier element
13 thermistor
14 adapter
16 temperature controller
20 piezoelectric ball
21 collimated beam
22 sensor electrode
23 sensitive film
31 sensor cell
32 electrode-holder base
33 sensor-cell cap
34 electrode holder
35 external electrode
36 tubing
41 moisture control module
42 detection module
43 measurement module
44 storage module
50, 51, 80, 81, 82 flow controller
52, 86 auto pressure regulator
53, 84 switching valve
54 dryer
(55, 56) moisture cell
55 permeation tube
56 Peltier unit
57 delay member
58 inlet
59 outlet
60 exhaust

The invention claimed is:

1. A standard-moisture generator comprising:
a flow controller configured to control a flow of a gas;
a dryer connected to the flow controller, configured to absorb water molecules in the gas and to generate a dry gas having a background moisture;
a moisture cell connected to the dryer, configured to add an object moisture to the dry gas; and
a delay member connected to the moisture cell, configured to pass the dry gas with a delay time depending on a concentration of the background moisture in the dry gas, wherein the delay member includes a metal tube made of stainless steel having an inner surface treated by electropolishing or electrochemical-buffing; and wherein the moisture cell includes a permeation tube configured to generate the object moisture and a Peltier unit configured to heat and to cool the permeation tube.

2. The standard-moisture generator of claim 1, wherein the delay member includes a metal-mesh filter made of stainless steel having a surface treated by electropolishing or electrochemical-buffing, configured to remove particles in the dry gas.

3. A system for detecting an abnormality in a standard-moisture, comprising:
a standard-moisture generator having:
a flow controller configured to control a flow of a gas,
a dryer connected to the flow controller, configured to absorb water molecules in the gas and to generate a dry gas having a background moisture,
a moisture cell connected to the dryer, configured to add an object moisture to the dry gas, and
a delay member connected to the moisture cell, configured to pass the dry gas with a delay time depending on a concentration of the background moisture in the dry gas;
a sensor unit having a ball surface-acoustic-wave sensor connected to an outlet of the delay member, configured to detect the moisture concentration in the dry gas; and
a processing unit having:
a moisture control module configured to regulate the flow controller and the moisture cell so as to flow the dry gas with the object moisture and the background moisture into the delay member,
a detection module configured to control the ball surface-acoustic-wave sensor to detect the moisture concentration in the dry gas, and
a measurement module configured to calculate the delay time using the moisture concentration in the dry gas,
wherein the moisture cell includes a permeation tube configured to generate the object moisture and a Peltier unit configured to heat and to cool the permeation tube.

4. The system of claim 3, wherein the delay member includes a metal tube made of stainless steel in which an inner surface is treated by electropolishing or electrochemical-buffing.

5. The system of claim 3, wherein the delay member includes a metal-mesh filter made of stainless steel having a surface treated by electropolishing or electrochemical-buffing, configured to remove particles in the dry gas.

6. A method for detecting an abnormality in a standard-moisture, using a standard-moisture generator having a flow controller, a dryer, a moisture cell and a delay member, and a ball surface-acoustic-wave sensor, comprising:
flowing a gas into the dryer by the flow controller so as to feed a dry gas having a background moisture;
removing water molecules on an inner surface of the delay member while a permeation tube in the moisture cell is cooled down to a temperature not to evaporate moisture from the permeation tube by a Peltier unit provided in the moisture cell;
generating an object moisture to be added to the dry gas by the moisture cell while the permeation tube is heated to a temperature to evaporate moisture by the Peltier unit;
passing the dry gas with the object moisture and the background moisture through the delay member;
measuring a delay time depending on a moisture concentration of the background moisture in the dry gas, the delay time is defined by a time between an onset of flowing the dry gas and a leading edge of a measured moisture concentration at one half of the object moisture; and
comparing a measured background moisture concentration to a reference,
wherein the moisture cell includes a permeation tube and a Peltier unit, and the object moisture is generated by heating a permeation tube.

7. The method of claim 6, further comprising, warning the abnormality when the measured background moisture concentration is not less than the reference.

8. The method of claim 6, wherein the delay member includes a metal tube made of stainless steel in which an inner surface is treated by electropolishing or electrochemical-buffing.

9. A computer program product for detecting an abnormality in a standard-moisture, driving a computer system including a standard-moisture generator having a flow controller, a dryer, a moisture cell and a delay member, and a ball surface-acoustic-wave sensor, comprising:
instructions to flow a gas into the dryer by the flow controller so as to feed a dry gas having a background moisture;
instructions to remove water molecules on an inner surface of the delay member while a permeation tube in the moisture cell is cooled down to a temperature not to evaporate moisture from the permeation tube by a Peltier unit provided in the moisture cell;
instructions to generate an object moisture to be added to the dry gas by the moisture cell while the permeation tube is heated to a temperature to evaporate moisture by the Peltier unit;
instructions to pass the dry gas with the object moisture and the background moisture through the delay member;
instructions to measure a delay time depending on a moisture concentration of the background moisture in the dry gas, the delay time is defined by a time between an onset of flowing the dry gas and a leading edge of a measured moisture concentration at one half of the object moisture; and
instructions to compare a measured background moisture concentration to a reference.

* * * * *